US012688909B2

(12) United States Patent
Li et al.

(10) Patent No.: US 12,688,909 B2
(45) Date of Patent: ***Jul. 21, 2026

(54) SYSTEM AND METHODS FOR UPSAMPLING OF DECOMPRESSED GENOMIC DATA AFTER LOSSY COMPRESSION USING A NEURAL NETWORK

(71) Applicant: AtomBeam Technologies Inc., Moraga, CA (US)

(72) Inventors: Zhu Li, Overland Park, KS (US); Brian Galvin, Silverdale, WA (US); Paras Maharjan, Kansas City, MO (US)

(73) Assignee: ATOMBEAM TECHNOLOGIES INC., Moraga, CA (US)

( * ) Notice: Subject to any disclaimer, the term of this patent is extended or adjusted under 35 U.S.C. 154(b) by 152 days.

This patent is subject to a terminal disclaimer.

(21) Appl. No.: 18/778,042

(22) Filed: Jul. 19, 2024

(65) Prior Publication Data

US 2025/0191697 A1      Jun. 12, 2025

Related U.S. Application Data

(63) Continuation of application No. 18/420,771, filed on Jan. 24, 2024, now Pat. No. 12,095,484, which is a continuation-in-part of application No. 18/410,980, filed on Jan. 11, 2024, now Pat. No. 12,068,761, which is a continuation-in-part of application No. 18/537,728, filed on Dec. 12, 2023, now Pat. No. 12,058,333.

(51) Int. Cl.
| | |
|---|---|
| *H03M 7/00* | (2006.01) |
| *G06N 3/0464* | (2023.01) |
| *G06N 3/048* | (2023.01) |
| *G16B 50/50* | (2019.01) |
| *H03M 7/30* | (2006.01) |

(52) U.S. Cl.
CPC ........... *G16B 50/50* (2019.02); *G06N 3/0464* (2023.01); *G06N 3/048* (2023.01); *H03M 7/3059* (2013.01); *H03M 7/70* (2013.01)

(58) Field of Classification Search
CPC ...... G16B 50/50; G06N 3/0464; G06N 3/048; G06N 3/0455; G06N 3/08; G06N 3/045; H03M 7/3059; H03M 7/70; H03M 7/6005; H04N 19/132; H04N 19/42; H04N 19/59; H04N 19/80; H04N 19/86
USPC ...................................................... 341/50, 51
See application file for complete search history.

(56) References Cited

U.S. PATENT DOCUMENTS

| | | | |
|---|---|---|---|
| 7,629,922 B2 | 12/2009 | Winstead et al. | |
| 7,876,257 B2 | 1/2011 | Vetro et al. | |
| 10,499,069 B2 | 12/2019 | Wang et al. | |
| 10,701,394 B1 * | 6/2020 | Caballero | ............ H04N 19/577 |

(Continued)

*Primary Examiner* — Jean B Jeanglaude
(74) *Attorney, Agent, or Firm* — GALVIN PATENT LAW LLC; Brian R. Galvin; Erin L. Johnston

(57) ABSTRACT

A system and methods for upsampling of decompressed biological data after lossy compression using a neural network integrates AI-based techniques to enhance compression quality. It incorporates a novel deep-learning neural network that upsamples decompressed data to restore information lost during lossy compression, taking advantage of cross-correlations between biological data sets.

11 Claims, 23 Drawing Sheets

100

(56)  References Cited

U.S. PATENT DOCUMENTS

| 11,656,353 | B2 | 5/2023 | Li et al. |
| 2022/0086463 | A1 | 3/2022 | Coban et al. |
| 2023/0154055 | A1 | 5/2023 | Besenbruch et al. |

* cited by examiner

Reconstructed
SAR I/Q
250

Pixel
Shuffle 4
240

B

Convolutional Layer

801 ∽ Receive a raw complex-valued SAR image

802 ∽ Preprocess the SAR image

803 ∽ Quantize the preprocessed SAR image

804 ∽ Compress the quantized SAR data

805 ∽ Compact the compressed SAR data

800

901   Receive a bit stream comprising compressed and compacted complex-valued SAR image data 902   De-compact the bit stream 903   Decompress the bit stream 904   Feed the de-compressed bit stream as input into a AI deblocking network 905   De-quantize the output of the AI deblocking network 906   Reconstruct the original complext-valued SAR image using the dequanized bit stream

900

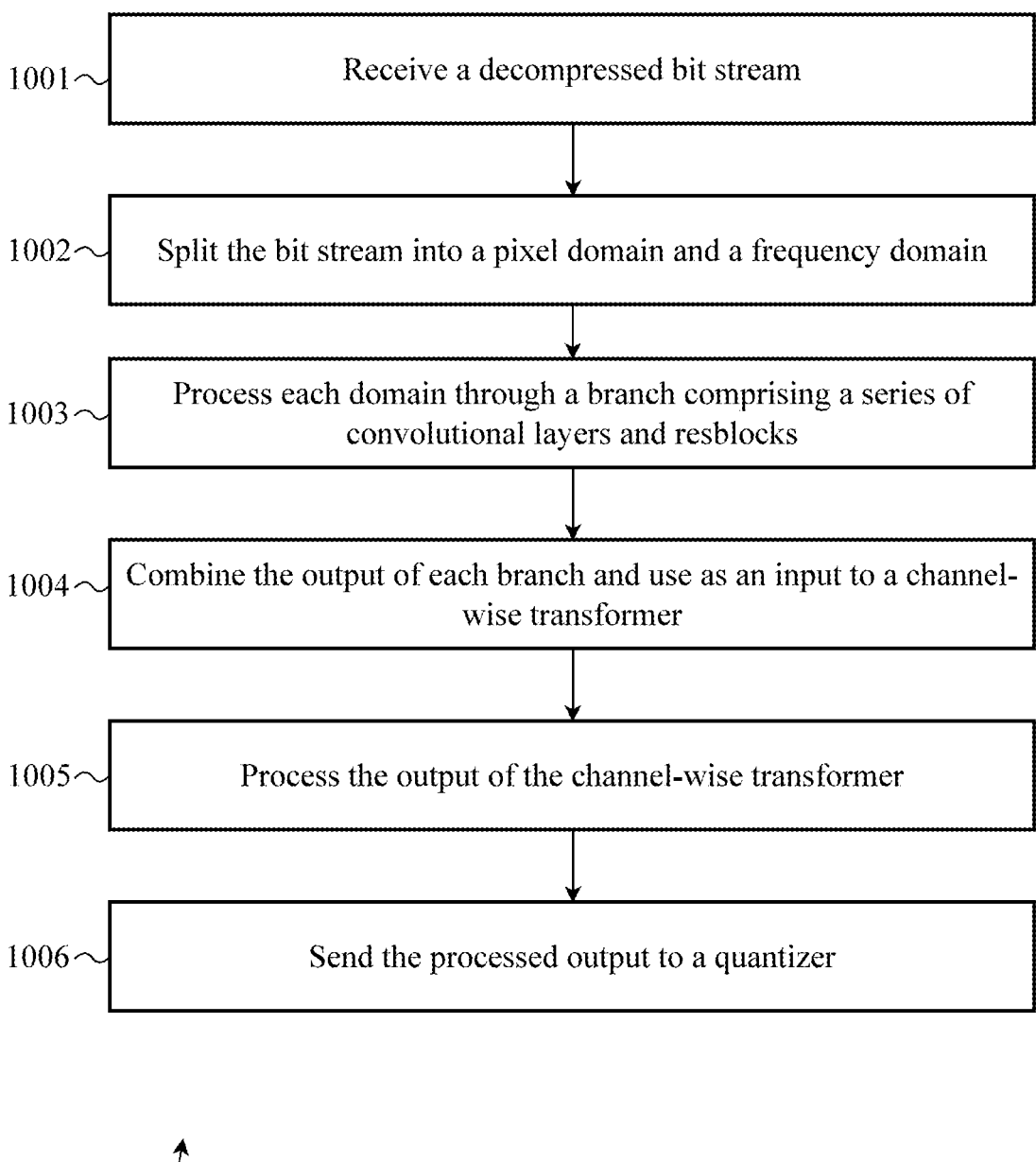

1001 ~| Receive a decompressed bit stream

1002 ~| Split the bit stream into a pixel domain and a frequency domain

1003 ~| Process each domain through a branch comprising a series of convolutional layers and resblocks 1004 ~| Combine the output of each branch and use as an input to a channel-wise transformer 1005 ~| Process the output of the channel-wise transformer 1006 ~| Send the processed output to a quantizer

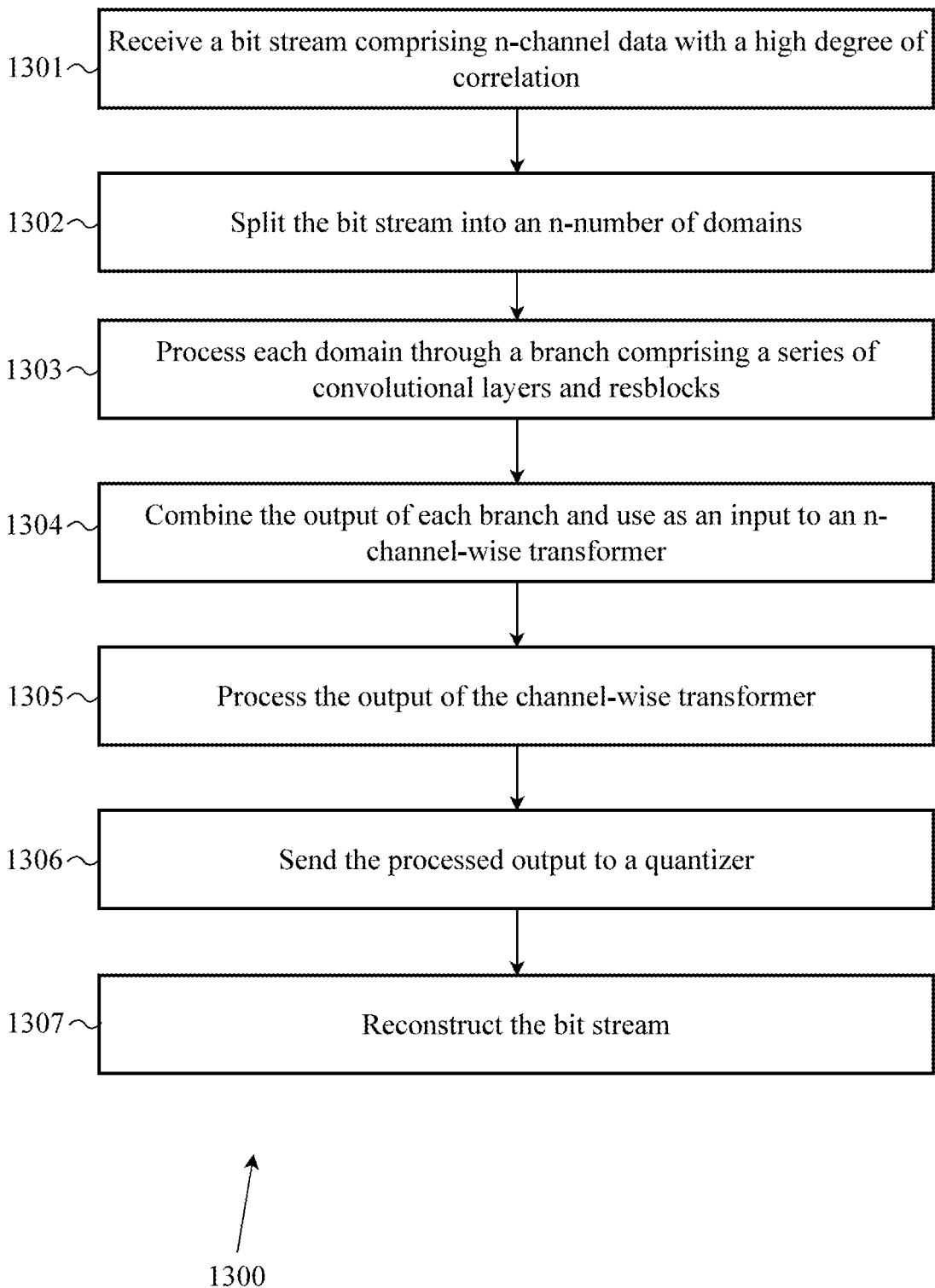

1301 — Receive a bit stream comprising n-channel data with a high degree of correlation 1302 — Split the bit stream into an n-number of domains 1303 — Process each domain through a branch comprising a series of convolutional layers and resblocks 1304 — Combine the output of each branch and use as an input to an n-channel-wise transformer 1305 — Process the output of the channel-wise transformer 1306 — Send the processed output to a quantizer 1307 — Reconstruct the bit stream

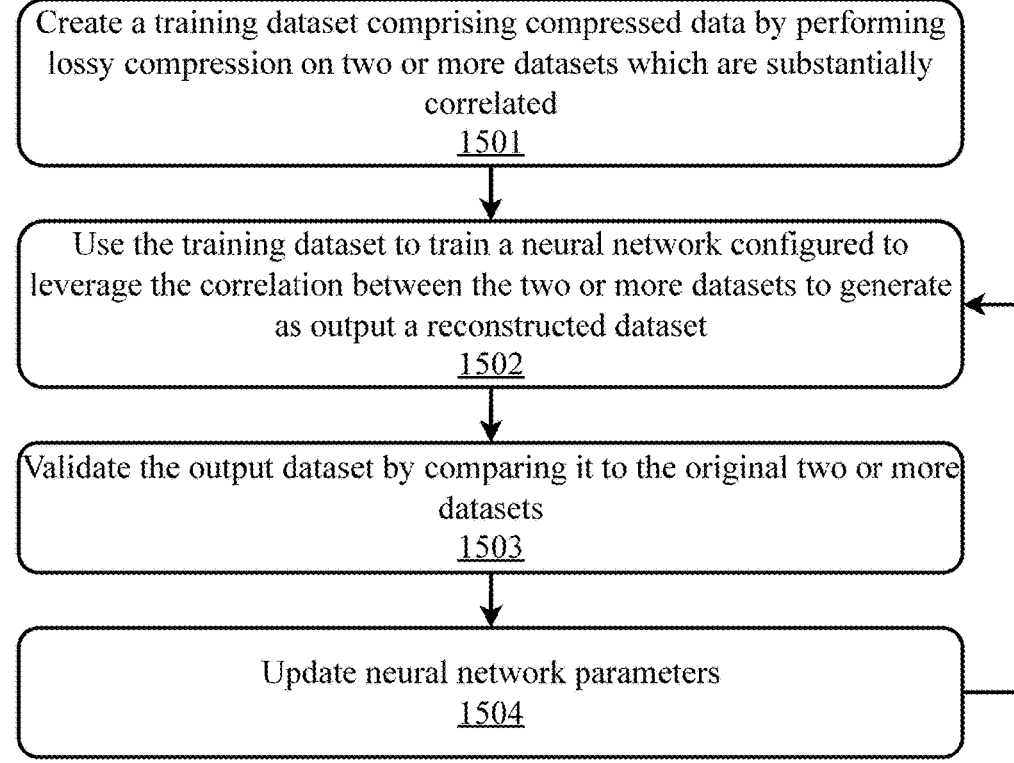

Create a training dataset comprising compressed data by performing lossy compression on two or more datasets which are substantially correlated
1501

Use the training dataset to train a neural network configured to leverage the correlation between the two or more datasets to generate as output a reconstructed dataset
1502

Validate the output dataset by comparing it to the original two or more datasets
1503

Update neural network parameters
1504

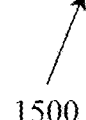

Receive compressed time-series data associated with an IoT data stream
1801

Perform lossy decompression on the time-series data
1802

Feed the decompressed time-series data into a neural upsampler configured to restore lost information
1803

Generate as output restored time-series data
1804

1800

SYSTEM AND METHODS FOR UPSAMPLING OF DECOMPRESSED GENOMIC DATA AFTER LOSSY COMPRESSION USING A NEURAL NETWORK

CROSS-REFERENCE TO RELATED APPLICATIONS

Priority is claimed in the application data sheet to the following patents or patent applications, each of which is expressly incorporated herein by reference in its entirety:
Ser. No. 18/420,771
Ser. No. 18/410,980
Ser. No. 18/537,728

BACKGROUND OF THE INVENTION

Field of the Art

The present invention is in the field of data compression, and more particularly is directed to the problem of recovering data lost from lossy compression and decompression.

Discussion of the State of the Art

For many applications, such as video compression for streaming video, lossy compression techniques such as HEVC (high-efficiency video coding) to optimize the use of available bandwidth and for other purposes. By definition, lossy compression involves the loss of some of the data being transmitted in the process of compression; in the video compression example, this results in lower-resolution video and provides the reason for pixelated video in low-bandwidth situations. Clearly it would be desirable to recover as much of the lost data as possible, but of course this is impossible in a single compressed channel for the method of compression results in a true loss of information.

Biological data is highly diverse and complex. As a concrete example, the information is encoded in DNA sequences, which can vary significantly among individuals and species. Creating a compression algorithm that effectively handles this diversity can be challenging. Balancing between lossless and lossy compression is a challenge. While lossless compression retains all the original information, it may not achieve high compression ratios. On the other hand, lossy compression may achieve higher ratios but at the cost of losing some information, which may be critical in genomics. As the volume of genomic data continues to increase with advances in sequencing technologies, the scalability of compression algorithms becomes crucial. Some algorithms may not scale well to handle the growing amount of data. Compressed genomic data should still be interpretable and accessible by researchers and clinicians. Ensuring that the compressed data retains its biological significance is important for downstream analyses.

What is needed is a system and methods for upsampling of decompressed biological data after lossy compression using a neural network.

SUMMARY OF THE INVENTION

Accordingly, the inventor has conceived and reduced to practice, a system and methods for upsampling of decompressed biological data after lossy compression using a neural network that integrates AI-based techniques to enhance compression quality. It incorporates a novel AI deblocking network composed of recurrent layers for feature extraction and a channel-wise transformer with attention to capture complex inter-channel dependencies. The recurrent layers extract multi-dimensional features from the two or more correlated datasets, while the channel-wise transformer learns global inter-channel relationships. This hybrid approach addresses both local and global features, mitigating compression artifacts and improving decompressed data quality. The model's outputs enable effective data reconstruction, achieving advanced compression while preserving crucial information for accurate analysis.

According to a preferred embodiment, a system for upsampling of decompressed biological data after lossy compression using a neural network is disclosed, comprising: a computing system comprising at least a memory and a processor; two or more datasets that are substantially correlated and which have been compressed with lossy compression, the two or more datasets comprising genomic data; a deep learning neural network configured to recover lost information associated with a compressed bit stream; and a decoder comprising a first plurality of programming instructions that, when operating on the processor, cause the computing system to: receive a compressed bit stream, the compressed bit stream comprising cross-correlated biological data; decompress each of the compressed bit stream; and use the decompressed bit stream as an input into the deep learning neural network to recover lost information associated with the genomic data.

According to another preferred embodiment, a method for upsampling of decompressed biological data after lossy compression using a neural network is disclosed, comprising the steps of: training a deep learning neural network to recover lost information associated with a compressed bit stream; receiving the compressed bit stream, the compressed bit stream comprising cross-correlated biological data; decompressing the compressed bit stream; and using the decompressed bit stream as an input into the deep learning neural network to recover information lost during lossy compression of the genomic data.

According to an aspect of an embodiment, the biological data comprises parallel datasets.

According to an aspect of an embodiment, the two or more datasets comprise biological data, such as genomic data, transcriptomic data, proteomic data, metabolomic data, epigenomic data, phenotypic data, clinical data, or any combination thereof.

According to an aspect of an embodiment, the biological data may be from a subset of the human genome, transcriptome, proteome, metabolome, or epigenome.

According to an aspect of an embodiment, the deep learning neural network is a neural network that can recover signals from a compressed bitstream.

According to an aspect of an embodiment, the compressed bit stream comprises a plurality of channels, wherein each of the plurality of channels is associated with a genomic dataset.

BRIEF DESCRIPTION OF THE DRAWING FIGURES

FIG. 10 is a flow diagram illustrating an exemplary method for deblocking using a trained deep learning algorithm, according to an embodiment.

FIG. 13 is a flow diagram illustrating an exemplary method for processing a compressed n-channel bit stream using an AI deblocking network, according to an embodiment.

FIG. 15 is a flow diagram illustrating an exemplary method for training a neural network to perform upsampling of decompressed data after lossy compression, according to an embodiment.

DETAILED DESCRIPTION OF THE INVENTION

Figure 1:
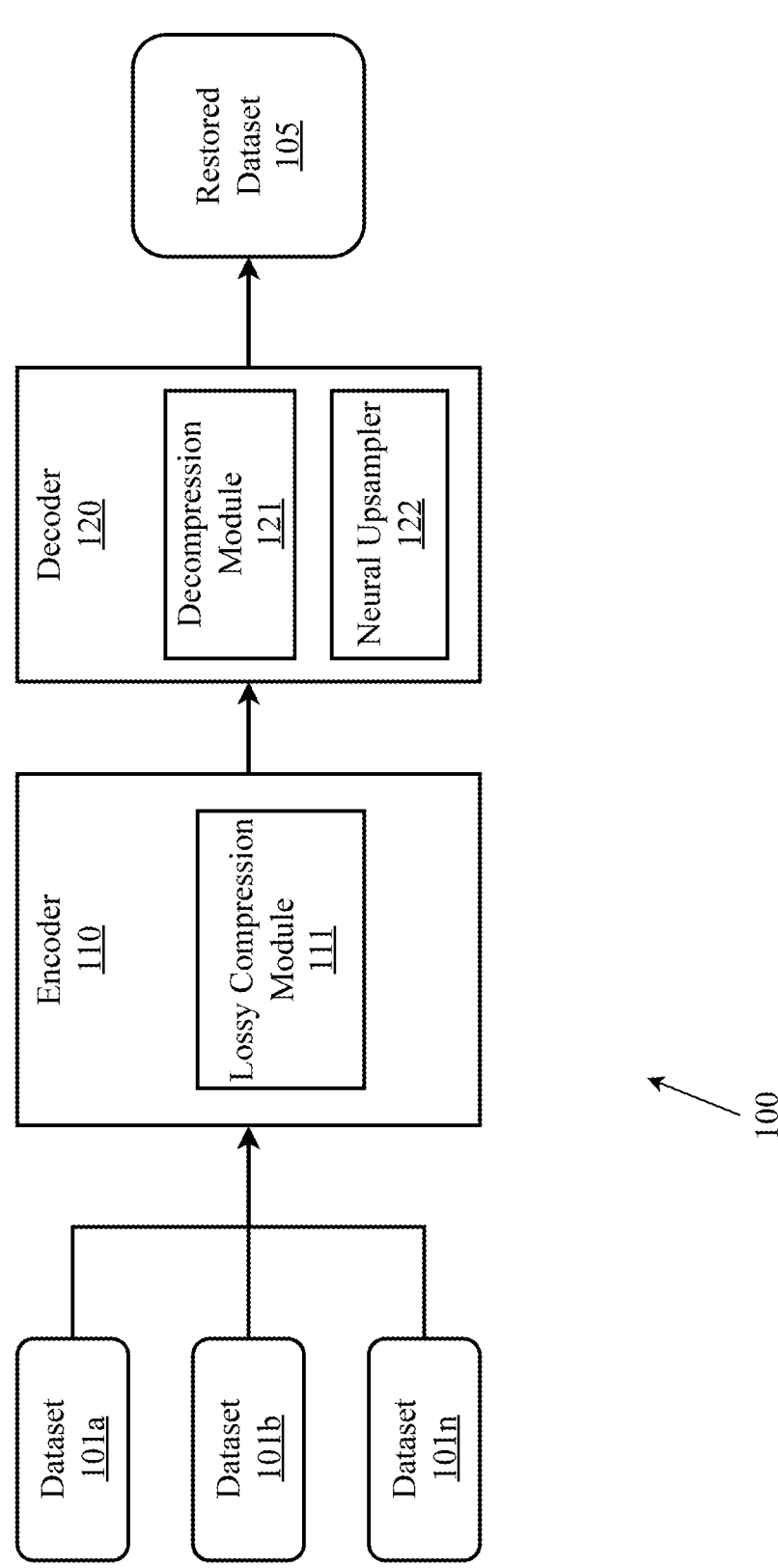
FIG. 1 is a block diagram illustrating an exemplary system architecture for upsampling of decompressed data after lossy compression using a neural network, according to an embodiment.

The inventor has conceived, and reduced to practice, a system and methods for upsampling of decompressed biological data after lossy compression using a neural network that integrates AI-based techniques to enhance compression quality. It incorporates a novel AI deblocking network composed of recurrent layers for feature extraction and a channel-wise transformer with attention to capture complex inter-channel dependencies. The recurrent layers extract multi-dimensional features from the two or more correlated datasets, while the channel-wise transformer learns global inter-channel relationships. This hybrid approach addresses both local and global features, mitigating compression artifacts and improving decompressed data quality. The model's outputs enable effective data reconstruction, achieving advanced compression while preserving crucial information for accurate analysis.

SAR images provide an excellent exemplary use case for a system and methods for upsampling of decompressed data after lossy compression. Synthetic Aperture Radar technology is used to capture detailed images of the Earth's surface by emitting microwave signals and measuring their reflections. Unlike traditional grayscale images that use a single intensity value per pixel, SAR images are more complex. Each pixel in a SAR image contains not just one value but a complex number (I+Qi). A complex number consists of two components: magnitude (or amplitude) and phase. In the context of SAR, the complex value at each pixel represents the strength of the radar signal's reflection (magnitude) and the phase shift (phase) of the signal after interacting with the terrain. This information is crucial for understanding the properties of the surface and the objects present. In a complex-value SAR image, the magnitude of the complex number indicates the intensity of the radar reflection, essentially representing how strong the radar signal bounced back from the surface. Higher magnitudes usually correspond to stronger reflections, which may indicate dense or reflective materials on the ground.

The complex nature of SAR images stems from the interference and coherence properties of radar waves. When radar waves bounce off various features on the Earth's surface, they can interfere with each other. This interference pattern depends on the radar's wavelength, the angle of incidence, and the distances the waves travel. As a result, the radar waves can combine constructively (amplifying the signal) or destructively (canceling out the signal). This interference phenomenon contributes to the complex nature of SAR images. The phase of the complex value encodes information about the distance the radar signal traveled and any changes it underwent during the round-trip journey. For instance, if the radar signal encounters a surface that's slightly elevated or depressed, the phase of the returning signal will be shifted accordingly. Phase information is crucial for generating accurate topographic maps and understanding the geometry of the terrain.

Coherence refers to the consistency of the phase relationship between different pixels in a SAR image. Regions with high coherence have similar phase patterns and are likely to represent stable surfaces or structures, while regions with low coherence might indicate changes or disturbances in the terrain.

Complex-value SAR image compression is important for several reasons such as data volume reduction, bandwidth and transmission efficiency, real-time applications, and archiving and retrieval. SAR images can be quite large due to their high resolution and complex nature. Compression helps reduce the storage and transmission requirements, making it more feasible to handle and process the data. When SAR images need to be transmitted over limited bandwidth channels, compression can help optimize data transmission and minimize communication costs. Some SAR applications, such as disaster response and surveillance, require real-time processing. Compressed data can be processed faster, enabling quicker decision-making. Additionally, compressed SAR images take up less storage space, making long-term archiving and retrieval more manageable.

According to various embodiments, a system is proposed which provides a novel pipeline for compressing and subsequently recovering complex-valued SAR image data using a prediction recovery framework that utilizes a conventional image compression algorithm to encode the original image to a bitstream. In an embodiment, a lossless compaction method may be applied to the encoded bitstream, further reducing the size of the SAR image data for both storage and transmission. Subsequently, the system decodes a prediction of the I/Q channels and then recovers the phase and amplitude via a deep-learning based network to effectively remove compression artifacts and recover information of the SAR image as part of the loss function in the training. The deep-learning based network may be referred to herein as an artificial intelligence (AI) deblocking network.

Deblocking refers to a technique used to reduce or eliminate blocky artifacts that can occur in compressed images or videos. These artifacts are a result of lossy compression algorithms, such as JPEG for images or various video codecs like H.264, H.265 (HEVC), and others, which divide the image or video into blocks and encode them with varying levels of quality. Blocky artifacts, also known as "blocking artifacts," become visible when the compression ratio is high, or the bitrate is low. These artifacts manifest as noticeable edges or discontinuities between adjacent blocks in the image or video. The result is a visual degradation characterized by visible square or rectangular regions, which can significantly reduce the overall quality and aesthetics of the content. Deblocking techniques are applied during the decoding process to mitigate or remove these artifacts. These techniques typically involve post-processing steps that smooth out the transitions between adjacent blocks, thus improving the overall visual appearance of the image or video. Deblocking filters are commonly used in video codecs to reduce the impact of blocking artifacts on the decoded video frames.

According to various embodiments, the disclosed system and methods may utilize a SAR recovery network configured to perform data deblocking during the data decoding process. Amplitude and phase images exhibit a non-linear relationship, while I and Q images demonstrate a linear relationship. The SAR recovery network is designed to leverage this linear relationship by utilizing the I/Q images to enhance the decoded SAR image. In an embodiment, the SAR recovery network is a deep learned neural network. According to an aspect of an embodiment, the SAR recovery network utilizes residual learning techniques. According to an aspect of an embodiment, the SAR recovery network comprises a channel-wise transformer with attention. According to an aspect of an embodiment, the SAR recovery network comprises Multi-Scale Attention Blocks (MSAB).

A channel-wise transformer with attention is a neural network architecture that combines elements of both the transformer architecture and channel-wise attention mechanisms. It's designed to process multi-channel data, such as SAR images, where each channel corresponds to a specific feature map or modality. The transformer architecture is a powerful neural network architecture initially designed for natural language processing (NLP) tasks. It consists of self-attention mechanisms that allow each element in a sequence to capture relationships with other elements, regardless of their position. The transformer has two main components: the self-attention mechanism (multi-head self-attention) and feedforward neural networks (position-wise feedforward layers). Channel-wise attention, also known as "Squeeze-and-Excitation" (SE) attention, is a mechanism commonly used in convolutional neural networks (CNNs) to model the interdependencies between channels (feature maps) within a single layer. It assigns different weights to different channels to emphasize important channels and suppress less informative ones. At each layer of the network, a channel-wise attention mechanism is applied to the input data. This mechanism captures the relationships between different channels within the same layer and assigns importance scores to each channel based on its contribution to the overall representation. After the channel-wise attention, a transformer-style self-attention mechanism is applied to the output of the channel-wise attention. This allows each channel to capture dependencies with other channels in a more global context, similar to how the transformer captures relationships between elements in a sequence. Following the transformer self-attention, feedforward neural network layers (position-wise feedforward layers) can be applied to further process the transformed data.

The system and methods described herein in various embodiments may be directed to the processing of audio data such as, for example, speech channels associated with one or more individuals.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Definitions

The term "bit" refers to the smallest unit of information that can be stored or transmitted. It is in the form of a binary digit (either 0 or 1). In terms of hardware, the bit is represented as an electrical signal that is either off (representing 0) or on (representing 1).

The term "codebook" refers to a database containing sourceblocks each with a pattern of bits and reference code unique within that library. The terms "library" and "encoding/decoding library" are synonymous with the term codebook.

The terms "compression" and "deflation" as used herein mean the representation of data in a more compact form than the original dataset. Compression and/or deflation may be either "lossless", in which the data can be reconstructed in its original form without any loss of the original data, or "lossy" in which the data can be reconstructed in its original form, but with some loss of the original data.

The terms "compression factor" and "deflation factor" as used herein mean the net reduction in size of the compressed data relative to the original data (e.g., if the new data is 70% of the size of the original, then the deflation/compression factor is 30% or 0.3.)

The terms "compression ratio" and "deflation ratio", and as used herein all mean the size of the original data relative to the size of the compressed data (e.g., if the new data is 70% of the size of the original, then the deflation/compression ratio is 70% or 0.7.)

The term "data set" refers to a grouping of data for a particular purpose. One example of a data set might be a word processing file containing text and formatting information. Another example of a data set might comprise data gathered/generated as the result of one or more radars in operation.

The term "sourcepacket" as used herein means a packet of data received for encoding or decoding. A sourcepacket may be a portion of a data set.

The term "sourceblock" as used herein means a defined number of bits or bytes used as the block size for encoding or decoding. A sourcepacket may be divisible into a number of sourceblocks. As one non-limiting example, a 1 megabyte sourcepacket of data may be encoded using 512 byte sourceblocks. The number of bits in a sourceblock may be dynamically optimized by the system during operation. In one aspect, a sourceblock may be of the same length as the block size used by a particular file system, typically 512 bytes or 4,096 bytes.

The term "codeword" refers to the reference code form in which data is stored or transmitted in an aspect of the system. A codeword consists of a reference code to a sourceblock in the library plus an indication of that sourceblock's location in a particular data set.

The term "deblocking" as used herein refers to a technique used to reduce or eliminate blocky artifacts that can occur in compressed images or videos. These artifacts are a result of lossy compression algorithms, such as JPEG for images or various video codecs like H.264, H.265 (HEVC), and others, which divide the image or video into blocks and encode them with varying levels of quality. Blocky artifacts, also known as "blocking artifacts," become visible when the compression ratio is high, or the bitrate is low. These artifacts manifest as noticeable edges or discontinuities between adjacent blocks in the image or video. The result is a visual degradation characterized by visible square or rectangular regions, which can significantly reduce the overall quality and aesthetics of the content. Deblocking techniques are applied during the decoding process to mitigate or remove these artifacts. These techniques typically involve post-processing steps that smooth out the transitions between adjacent blocks, thus improving the overall visual appearance of the image or video. Deblocking filters are commonly used in video codecs to reduce the impact of blocking artifacts on the decoded video frames. A primary goal of deblocking is to enhance the perceptual quality of the compressed content, making it more visually appealing to viewers. It's important to note that deblocking is just one of many post-processing steps applied during the decoding and playback of compressed images and videos to improve their quality.

Conceptual Architecture

FIG. 1 is a block diagram illustrating an exemplary system architecture 100 for upsampling of decompressed data after lossy compression using a neural network, according to an embodiment. According to the embodiment, the system 100 comprises an encoder module 110 configured to receive two or more datasets 101a-n which are substantially correlated and perform lossy compression on the received dataset, and a decoder module 120 configured to receive a compressed bit stream and use a trained neural network to output a reconstructed dataset which can restore most of the "lost" data due to the lossy compression. Datasets 101a-n may comprise streaming data or data received in a batch format. Datasets 101a-n may comprise one or more datasets, data streams, data files, or various other types of data structures which may be compressed. Furthermore, dataset 101a-n may comprise n-channel data comprising a plurality of data channels sent via a single data stream.

Encoder 110 may utilize a lossy compression module 111 to perform lossy compression on a received dataset 101a-n. The type of lossy compression implemented by lossy compression module 111 may be dependent upon the data type being processed. For example, for SAR imagery data, High Efficiency Video Coding (HEVC) may be used to compress the dataset. In another example, if the data being processed is time-series data, then delta encoding may be used to compress the dataset. The encoder 110 may then send the compressed data as a compressed data stream to a decoder 120 which can receive the compressed data stream and decompress the data using a decompression module 121.

The decompression module 121 may be configured to perform data decompression a compressed data stream using an appropriate data decompression algorithm. The decompressed data may then be used as input to a neural upsampler 122 which utilizes a trained neural network to restore decompressed data to nearly its original state 105 by taking advantage of the information embedded in the correlation between the two or more datasets 101a-n.

Figure 2A:
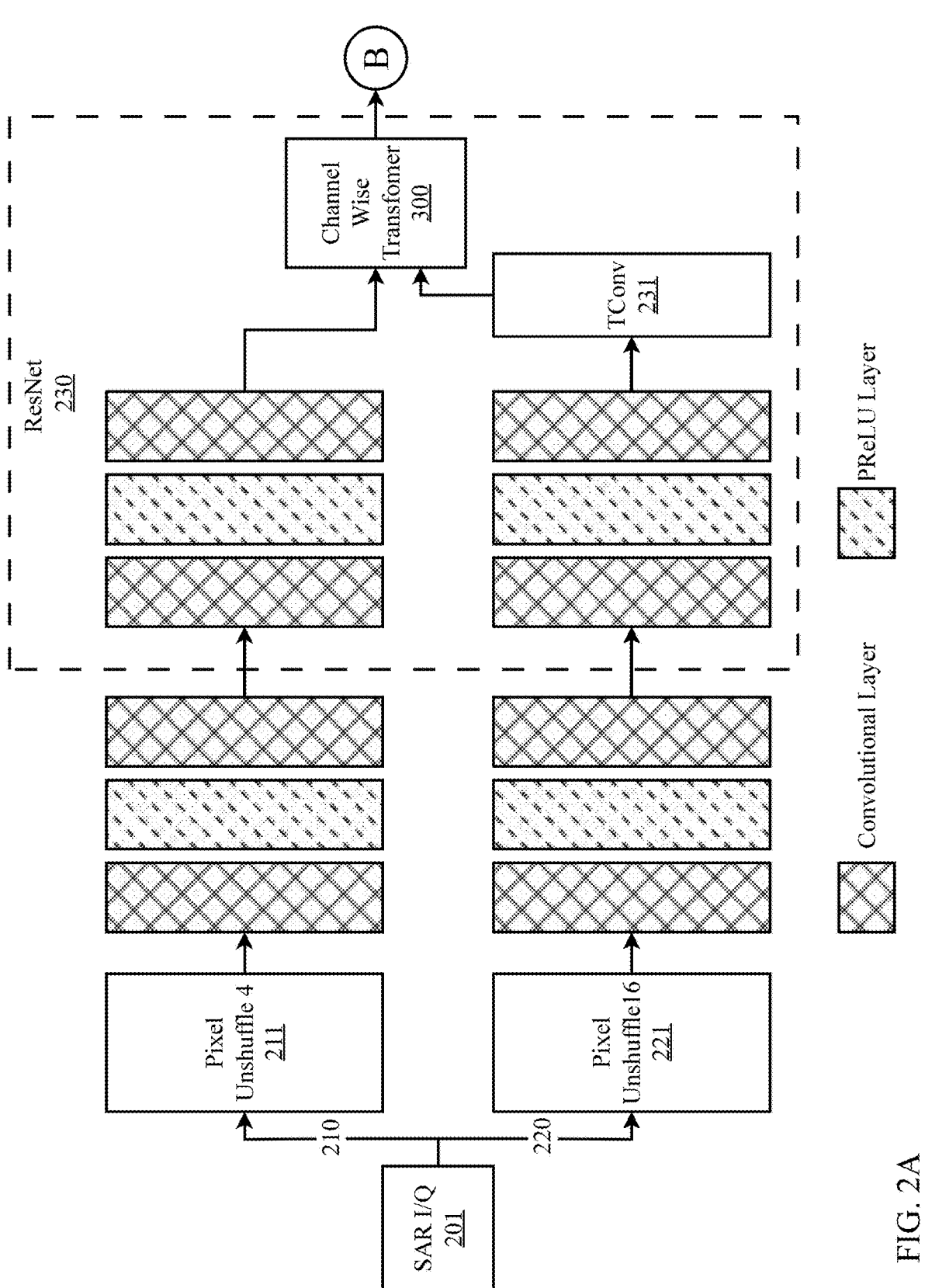
FIGS. 2A and 2B illustrate an exemplary architecture for an AI deblocking network configured to provide deblocking on dual-channel data stream comprising SAR I/Q data, according to an embodiment.
Figure 2B:
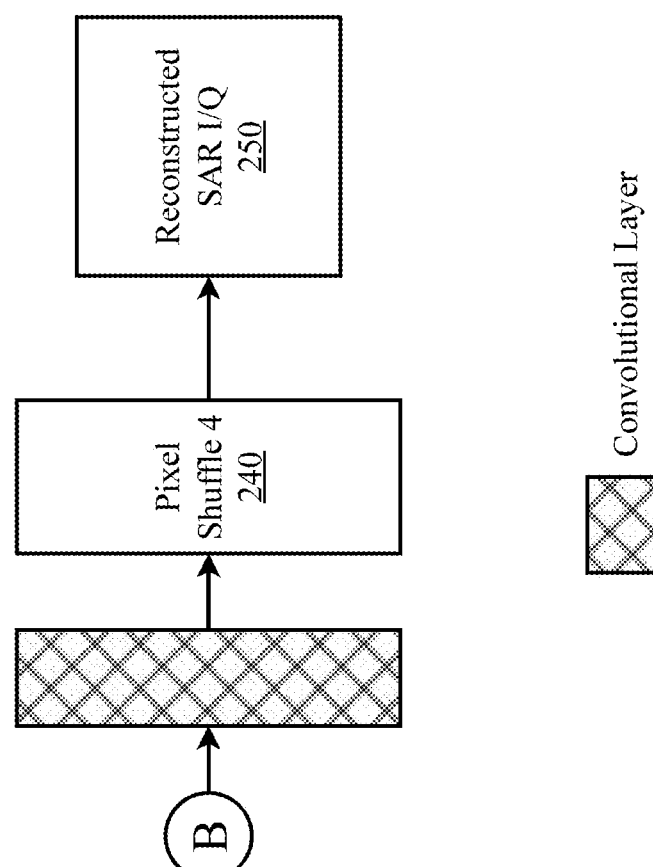

FIGS. 2A and 2B illustrate an exemplary architecture for an AI deblocking network configured to provide deblocking for dual-channel data stream comprising SAR I/Q data, according to an embodiment. In the context of this disclosure, dual-channel data refers to fact that SAR image signal can be represented as two (dual) components (i.e., I and Q) which are correlated to each other in some manner. In the case of I and Q, their correlation is that they can be transformed into phase and amplitude information and vice versa. AI deblocking network utilizes a deep learned neural network architecture for joint frequency and pixel domain learning. According to the embodiment, a network may be developed for joint learning across one or more domains. As shown, the top branch 210 is associated with the pixel domain learning and the bottom branch 220 is associated with the frequency domain learning. According to the embodiment, the AI deblocking network receives as input complex-valued SAR image I and Q channels 201 which, having been encoded via encoder 110, has subsequently been decompressed via decoder 120 before being passed to AI deblocking network for image enhancement via artifact removal. Inspired by the residual learning network and the MSAB attention mechanism, AI deblocking network employs resblocks that take two inputs. In some implementations, to reduce complexity the spatial resolution may be downsampled to one-half and one-fourth. During the final reconstruction the data may be upsampled to its original resolution. In one implementation, in addition to downsampling, the network employs deformable convolution to extract initial features, which are then passed to the resblocks. In an embodiment, the network comprises one or more resblocks and one or more convolutional filters. In an embodiment, the network comprises 8 resblocks and 64 convolutional filters.

Deformable convolution is a type of convolutional operation that introduces spatial deformations to the standard convolutional grid, allowing the convolutional kernel to adaptively sample input features based on the learned offsets. It's a technique designed to enhance the modeling of spatial relationships and adapt to object deformations in computer vision tasks. In traditional convolutional operations, the kernel's positions are fixed and aligned on a regular grid across the input feature map. This fixed grid can limit the ability of the convolutional layer to capture complex transformations, non-rigid deformations, and variations in object appearance. Deformable convolution aims to address this limitation by introducing the concept of spatial deformations. Deformable convolution has been particularly effective in tasks like object detection and semantic segmentation, where capturing object deformations and accurately localizing object boundaries are important. By allowing the convolutional kernels to adaptively sample input features from different positions based on learned offsets, deformable convolution can improve the model's ability to handle complex and diverse visual patterns.

According to an embodiment, the network may be trained as a two stage process, each utilizing specific loss functions. During the first stage, a mean squared error (MSE) function is used in the I/Q domain as a primary loss function for the AI deblocking network. The loss function of the SAR I/Q channel $L_{SAR}$ is defined as:

$$L_{SAR} = \mathbb{E}[\|I - I_{amp}\|_2]$$

Moving to the second stage, the network reconstructs the amplitude component and computes the amplitude loss using MSE as follows:

$$L_{amp} = \mathbb{E}[\|I_{amp} - I_{dec,amp}\|_2]$$

To calculate the overall loss, the network combines the SAR loss and the amplitude loss, incorporating a weighting factor, a, for the amplitude loss. The total loss is computed as:

$$L_{total} = L_{SAR} + \alpha \times L_{amp}$$

The weighting factor value may be selected based on the dataset used during network training. In an embodiment, the network may be trained using two different SAR datasets: the National Geospatial-Intelligence Agency (NGA) SAR dataset and the Sandia National Laboratories Mini SAR Complex Imagery dataset, both of which feature complex-valued SAR images. In an embodiment, the weighting factor is set to 0.0001 for the NGA dataset and 0.00005 for the Sandia dataset. By integrating both the SAR and amplitude losses in the total loss function, the system effectively guides the training process to simultaneously address the removal of the artifacts and maintain the fidelity of the amplitude information. The weighting factor, α, enables AI deblocking network to balance the importance of the SAR loss and the amplitude loss, ensuring comprehensive optimization of the network during the training stages. In some implementations, diverse data augmentation techniques may be used to enhance the variety of training data. For example, techniques such as horizontal and vertical flops and rotations may be implemented on the training dataset. In an embodiment, model optimization is performed using MSE loss and Adam optimizer with a learning rate initially set to $1 \times 10^{-4}$ and decreased by a factor of 2 at epochs 100, 200, and 250, with a total of 300 epochs. In an implementation, the batch size is set to 256×256 with each batch containing 16 images.

Both branches first pass through a pixel unshuffling layer 211, 221 which implements a pixel unshuffling process on the input data. Pixel unshuffling is a process used in image processing to reconstruct a high-resolution image from a low-resolution image by rearranging or "unshuffling" the pixels. The process can involve the following steps, low-resolution input, pixel arrangement, interpolation, and enhancement. The input to the pixel unshuffling algorithm is a low-resolution image (i.e., decompressed, quantized SAR I/Q data). This image is typically obtained by downscaling a higher-resolution image such as during the encoding process executed by encoder 110. Pixel unshuffling aims to estimate the original high-resolution pixel values by redistributing and interpolating the low-resolution pixel values. The unshuffling process may involve performing interpolation techniques, such as nearest-neighbor, bilinear, or more sophisticated methods like bicubic or Lanczos interpolation, to estimate the missing pixel values and generate a higher-resolution image.

The output of the unshuffling layers 211, 221 may be fed into a series of layers which can include one or more convolutional layers and one or more parametric rectified linear unit (PRELU) layers. A legend is depicted for both FIG. 2A and FIG. 2B which indicates the cross hatched block represents a convolutional layer and the dashed block represents a PRELU layer. Convolution is the first layer to extract features from an input image. Convolution preserves the relationship between pixels by learning image features using small squares of input data. It is a mathematical operation that takes two inputs such as an image matrix and a filter or kernel. The embodiment features a cascaded ResNet-like structure comprising 8 ResBlocks to effectively process the input data. The filter size associated with each convolutional layer may be different. The filter size used for the pixel domain of the top branch may be different than the filter size used for the frequency domain of the bottom branch.

A PRELU layer is an activation function used in neural networks. The PRELU activation function extends the ReLU by introducing a parameter that allows the slope for negative values to be learned during training. The advantage of PRELU over ReLU is that it enables the network to capture more complex patterns and relationships in the data. By allowing a small negative slope for the negative inputs, the PRELU can learn to handle cases where the output should not be zero for all negative values, as is the case with the standard ReLU. In other implementations, other non-linear functions such as tanh or sigmoid can be used instead of PReLU.

After passing through a series of convolutional and PRELU layers, both branches enter the resnet 230 which further comprises more convolutional and PRELU layers. The frequency domain branch is slightly different than the pixel domain branch once inside ResNet 230, specifically the frequency domain is processed by a transposed convolutional (TConv) layer 231. Transposed convolutions are a type of operation used in neural networks for tasks like image generation, image segmentation, and upsampling. They are used to increase the spatial resolution of feature maps while maintaining the learned relationships between features. Transposed convolutions aim to increase spatial dimensions of feature maps, effectively "upsampling" them. This is typically done by inserting zeros (or other values) between existing values to create more space for new values.

Inside ResBlock 230 the data associated with the pixel and frequency domains are combined back into a single stream by using the output of the Tconv 231 and the output of the top branch. The combined data may be used as input for a channel-wise transformer 300. In some embodiments, the channel-wise transformer may be implemented as a multi-scale attention block utilizing the attention mechanism. For more detailed information about the architecture and functionality of channel-wise transformer 300 refer to FIG. 3. The output of channel-wise transformer 300 may be a bit stream suitable for reconstructing the original SAR I/Q image. FIG. 2B shows the output of ResBlock 230 is passed through a final convolutional layer before being processed by a pixel shuffle layer 240 which can perform upsampling on the data prior to image reconstruction. The output of the AI deblocking network may be passed through a quantizer 124 for dequantization prior to producing a reconstructed SAR I/Q image 250.

Figure 3:
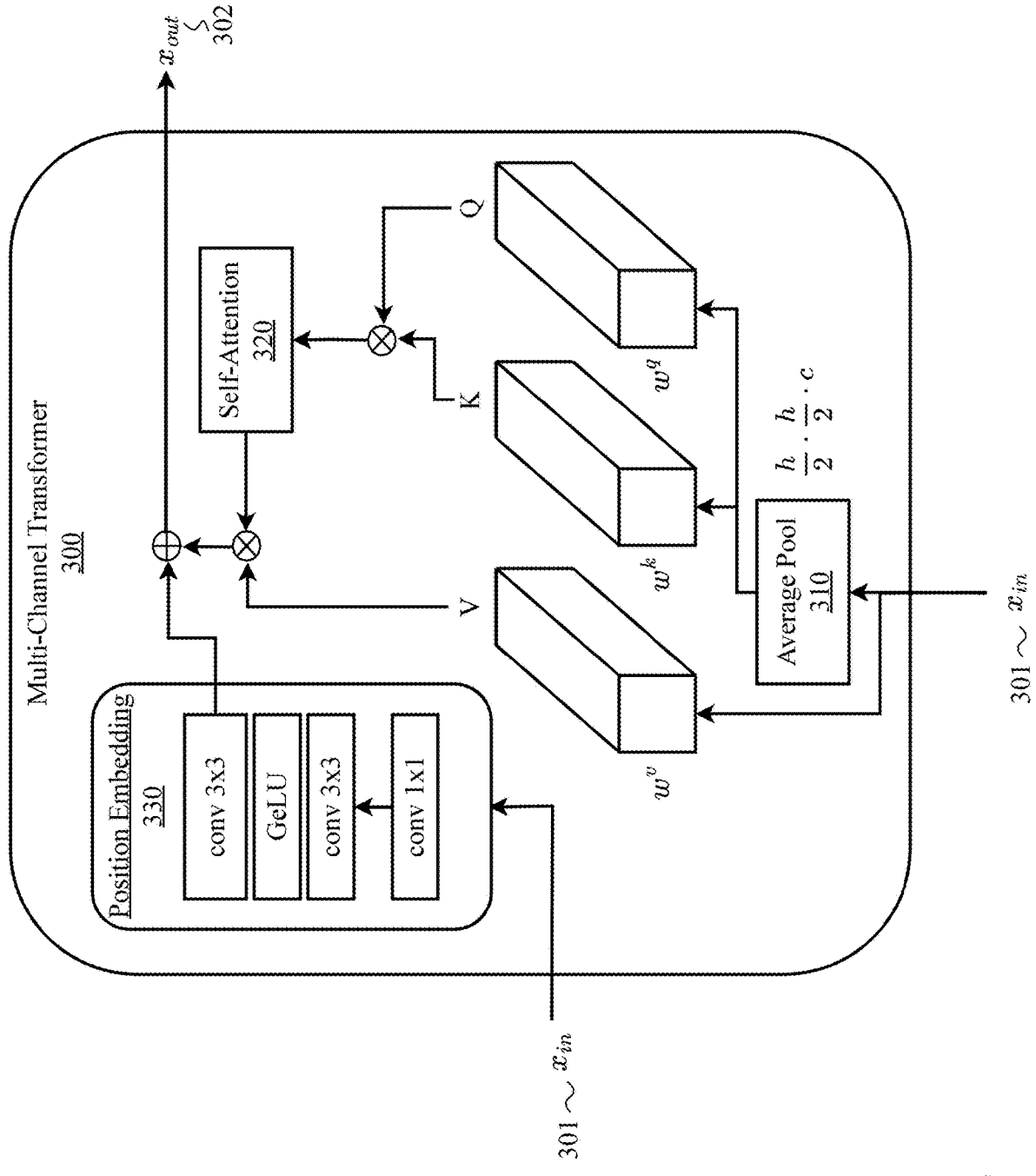
FIG. 3 is a block diagram illustrating an exemplary architecture for a component of the system for SAR image compression, the channel-wise transformer.

FIG. 3 is a block diagram illustrating an exemplary architecture for a component of the system for SAR image compression, the channel-wise transformer 300. According to the embodiment, channel-wise transformer receives an input signal, Xin 301, the input signal comprising SAR I/Q data which is being processed by AI deblocking network 123. The input signal may be copied and follow two paths through multi-channel transformer 300.

A first path may process input data through a position embedding module 330 comprising series of convolutional layers as well as a Gaussian Error Linear Unit (GeLU). In traditional recurrent neural networks or convolutional neural networks, the order of input elements is inherently encoded through the sequential or spatial nature of these architectures. However, in transformer-based models, where the attention mechanism allows for non-sequential relationships between tokens, the order of tokens needs to be explicitly conveyed to the model. Position embedding module 330 may represent a feedforward neural network (position-wise feedforward layers) configured to add position embeddings to the input data to convey the spatial location or arrangement of pixels in an image. The output of position embedding module 330 may be added to the output of the other processing path the received input signal is processed through.

A second path may process the input data. It may first be processed via a channel-wise configuration and then through a self-attention layer 320. The signal may be copied/duplicated such that a copy of the received signal is passed through an average pool layer 310 which can perform a downsampling operation on the input signal. It may be used to reduce the spatial dimensions (e.g., width and height) of feature maps while retaining the most important information. Average pooling functions by dividing the input feature map into non-overlapping rectangular or square regions (often referred to as pooling windows or filters) and replacing each region with the average of the values within that region. This functions to downsample the input by summarizing the information within each pooling window.

Self-attention layer 320 may be configured to provide an attention to AI deblocking network 123. The self-attention mechanism, also known as intra-attention or scaled dot-product attention, is a fundamental building block used in various deep learning models, particularly in transformer-based models. It plays a crucial role in capturing contextual relationships between different elements in a sequence or set of data, making it highly effective for tasks involving sequential or structured data like complex-valued SAR I/Q channels. Self-attention layer 320 allows each element in the input sequence to consider other elements and weigh their importance based on their relevance to the current element. This enables the model to capture dependencies between elements regardless of their positional distance, which is a limitation in traditional sequential models like RNNs and LSTMs.

The input 301 and downsampled input sequence is transformed into three different representations: Query (Q), Key (K), and Value (V). These transformations ($w^V$, $w^K$, and $w^Q$) are typically linear projections of the original input. For each element in the sequence, the dot product between its Query and the Keys of all other elements is computed. The dot products are scaled by a factor to control the magnitude of the attention scores. The resulting scores may be normalized using a softmax function to get attention weights that represent the importance of each element to the current element. The Values (V) of all elements are combined using the attention weights as coefficients. This produces a weighted sum, where elements with higher attention weights contribute more to the final representation of the current element. The weighted sum is the output of the self-attention mechanism for the current element. This output captures contextual information from the entire input sequence.

The output of the two paths (i.e., position embedding module 330 and self-attention layer 320) may be combined into a single output data stream $x_{out}$ 302.

Figure 4:
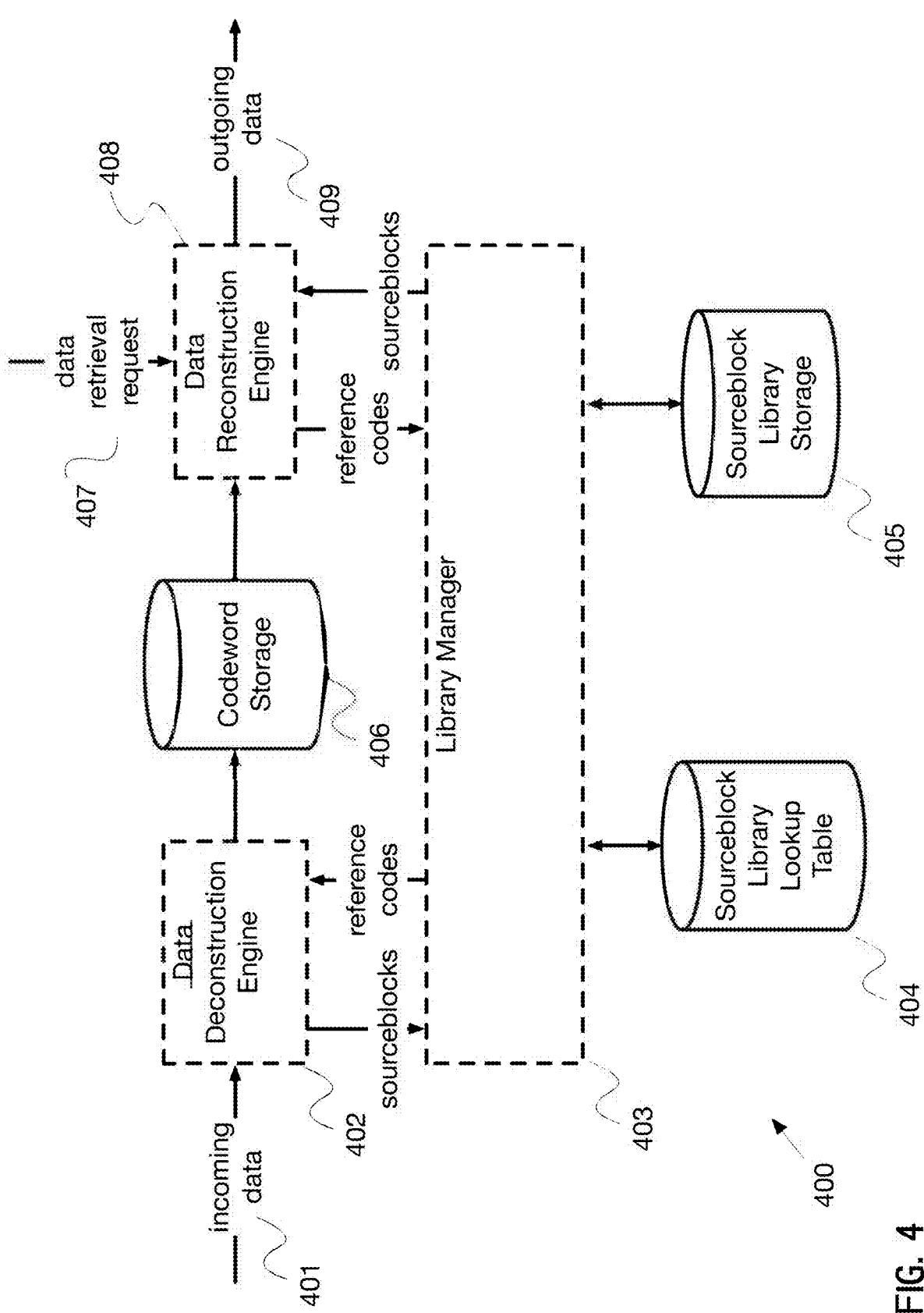
FIG. 4 is a block diagram illustrating an exemplary system architecture for providing lossless data compaction, according to an embodiment.

FIG. 4 is a block diagram illustrating an exemplary system architecture 400 for providing lossless data compaction, according to an embodiment. As incoming data 401 is received by data deconstruction engine 402. Data deconstruction engine 402 breaks the incoming data into sourceblocks, which are then sent to library manager 403. Using the information contained in sourceblock library lookup table 404 and sourceblock library storage 405, library manager 403 returns reference codes to data deconstruction engine 402 for processing into codewords, which are stored in codeword storage 106. When a data retrieval request 407 is received, data reconstruction engine 408 obtains the codewords associated with the data from codeword storage 406, and sends them to library manager 403. Library manager 403 returns the appropriate sourceblocks to data reconstruction engine 408, which assembles them into the proper order and sends out the data in its original form 409.

Figure 5:
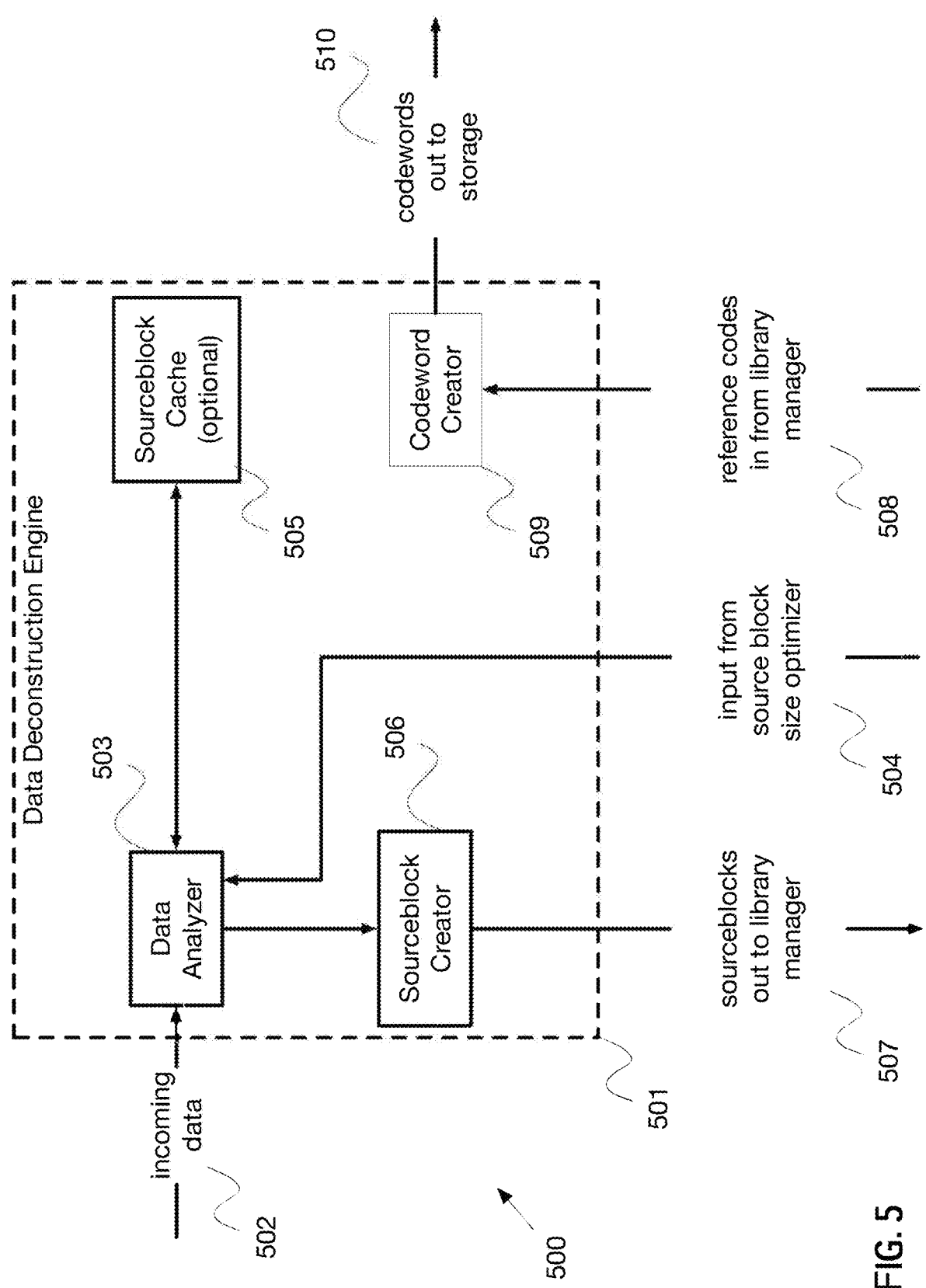
FIG. 5 is a diagram showing an embodiment of one aspect of the lossless data compaction system, specifically data deconstruction engine.

FIG. 5 is a diagram showing an embodiment of one aspect 500 of the system, specifically data deconstruction engine 501. Incoming data 502 is received by data analyzer 503, which optimally analyzes the data based on machine learning algorithms and input 504 from a sourceblock size optimizer, which is disclosed below. Data analyzer may optionally have access to a sourceblock cache 505 of recently processed sourceblocks, which can increase the speed of the system by avoiding processing in library manager 403. Based on information from data analyzer 503, the data is broken into sourceblocks by sourceblock creator

506, which sends sourceblocks 507 to library manager 403 for additional processing. Data deconstruction engine 501 receives reference codes 508 from library manager 403, corresponding to the sourceblocks in the library that match the sourceblocks sent by sourceblock creator 506, and codeword creator 509 processes the reference codes into codewords comprising a reference code to a sourceblock and a location of that sourceblock within the data set. The original data may be discarded, and the codewords representing the data are sent out to storage 510.

Figure 6:
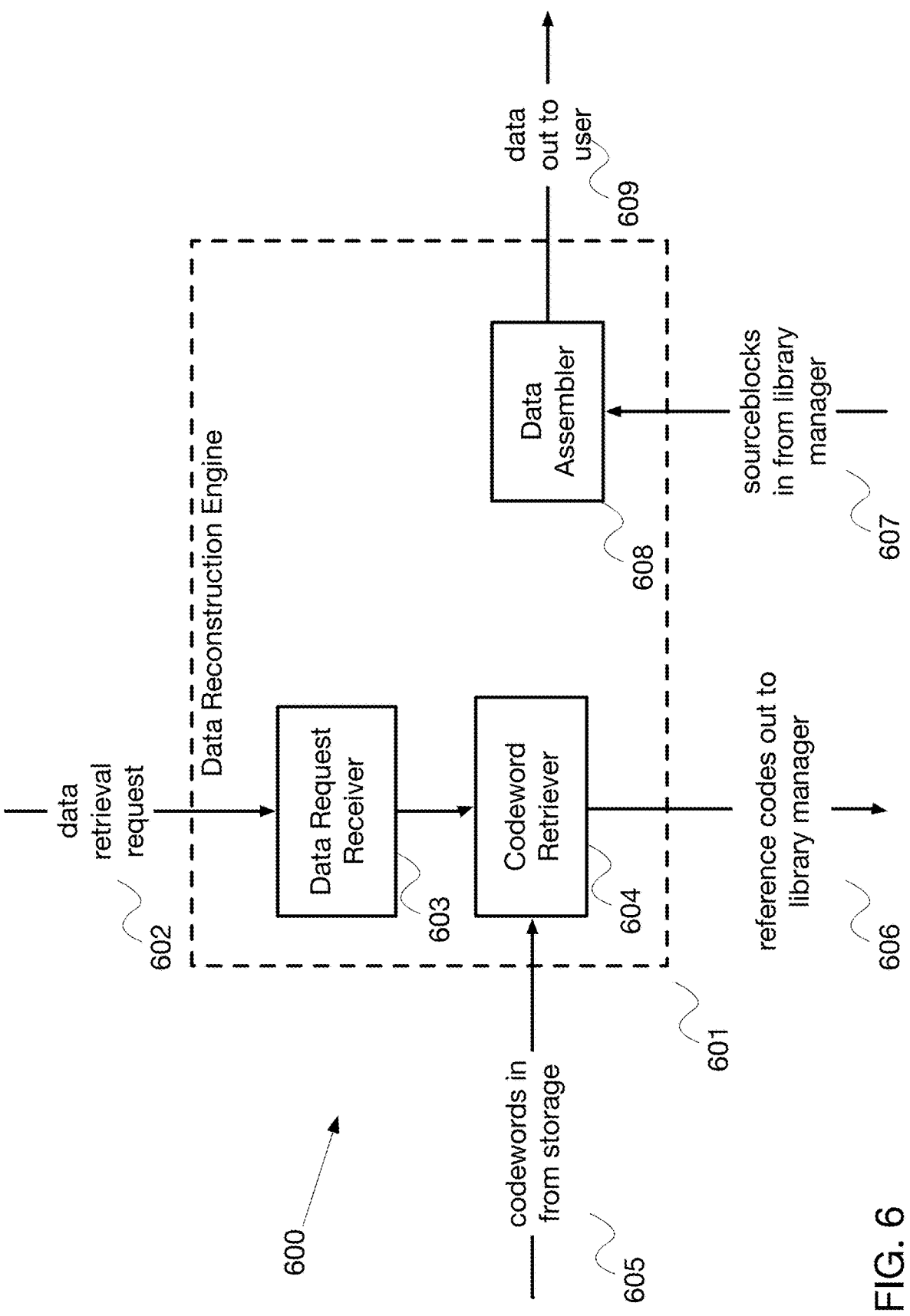
FIG. 6 is a diagram showing an embodiment of another aspect of lossless data compaction system, specifically data reconstruction engine.

FIG. 6 is a diagram showing an embodiment of another aspect of system 600, specifically data reconstruction engine 601. When a data retrieval request 602 is received by data request receiver 603 (in the form of a plurality of codewords corresponding to a desired final data set), it passes the information to data retriever 604, which obtains the requested data 605 from storage. Data retriever 604 sends, for each codeword received, a reference codes from the codeword 606 to library manager 403 for retrieval of the specific sourceblock associated with the reference code. Data assembler 608 receives the sourceblock 607 from library manager 403 and, after receiving a plurality of sourceblocks corresponding to a plurality of codewords, assembles them into the proper order based on the location information contained in each codeword (recall each codeword comprises a sourceblock reference code and a location identifier that specifies where in the resulting data set the specific sourceblock should be restored to. The requested data is then sent to user 609 in its original form.

Figure 7:
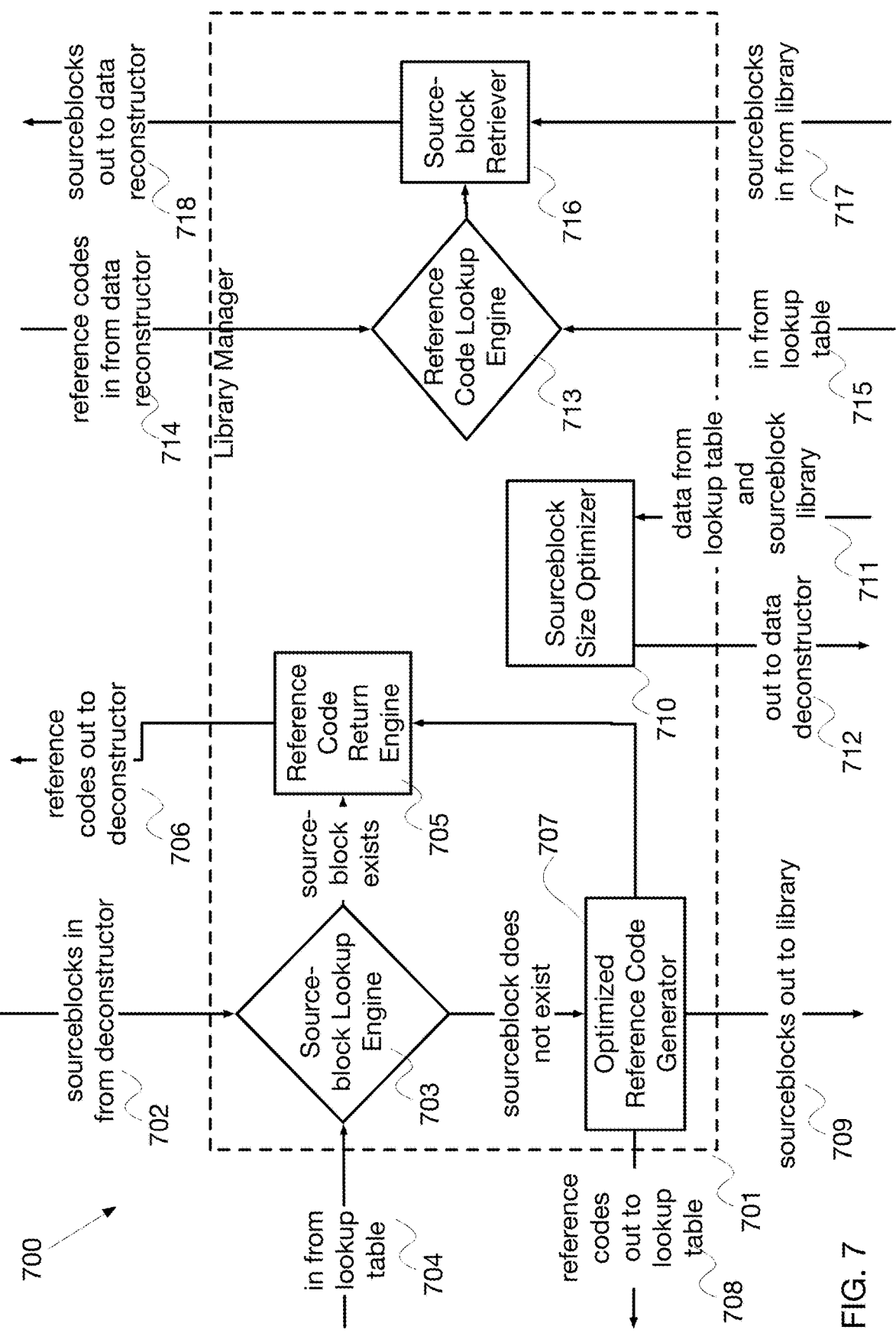
FIG. 7 is a diagram showing an embodiment of another aspect of lossless data compaction the system, specifically library manager.

FIG. 7 is a diagram showing an embodiment of another aspect of the system 700, specifically library manager 701. One function of library manager 701 is to generate reference codes from sourceblocks received from data deconstruction engine 701. As sourceblocks are received 702 from data deconstruction engine 501, sourceblock lookup engine 703 checks sourceblock library lookup table 704 to determine whether those sourceblocks already exist in sourceblock library storage 705. If a particular sourceblock exists in sourceblock library storage 105, reference code return engine 705 sends the appropriate reference code 706 to data deconstruction engine 601. If the sourceblock does not exist in sourceblock library storage 105, optimized reference code generator 407 generates a new, optimized reference code based on machine learning algorithms. Optimized reference code generator 707 then saves the reference code 708 to sourceblock library lookup table 704; saves the associated sourceblock 709 to sourceblock library storage 105; and passes the reference code to reference code return engine 705 for sending 706 to data deconstruction engine 501. Another function of library manager 701 is to optimize the size of sourceblocks in the system. Based on information 711 contained in sourceblock library lookup table 404, sourceblock size optimizer 410 dynamically adjusts the size of sourceblocks in the system based on machine learning algorithms and outputs that information 712 to data analyzer 603. Another function of library manager 701 is to return sourceblocks associated with reference codes received from data reconstruction engine 601. As reference codes are received 714 from data reconstruction engine 601, reference code lookup engine 713 checks sourceblock library lookup table 715 to identify the associated sourceblocks; passes that information to sourceblock retriever 716, which obtains the sourceblocks 717 from sourceblock library storage 405; and passes them 718 to data reconstruction engine 601.

Detailed Description of Exemplary Aspects

Figure 8:
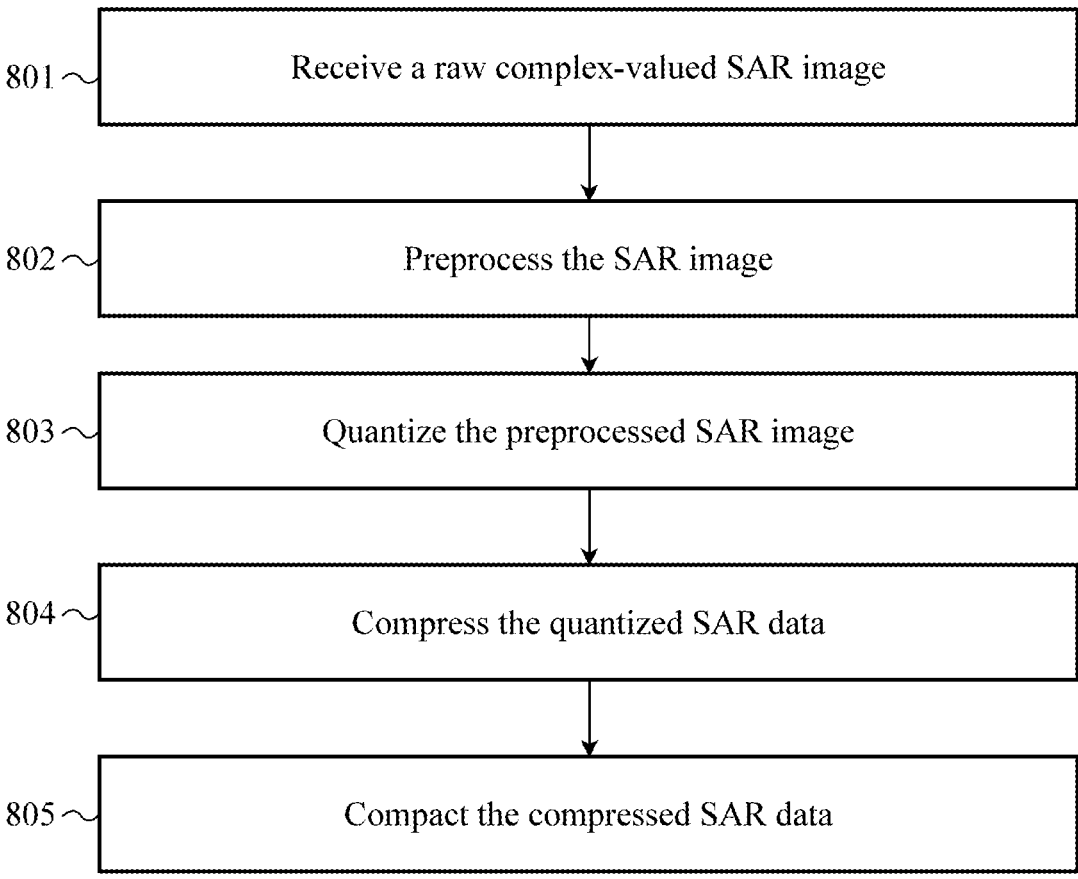
FIG. 8 is a flow diagram illustrating an exemplary method for complex-valued SAR image compression, according to an embodiment.

FIG. 8 is a flow diagram illustrating an exemplary method 800 for complex-valued SAR image compression, according to an embodiment. According to the embodiment, the process begins at step 801 when encoder 110 receives a raw complex-valued SAR image. The complex-valued SAR image comprises both I and Q components. In some embodiments, the I and Q components may be processed as separate channels. At step 802, the received SAR image may be preprocessed for further processing by encoder 110. For example, the input image may be clipped or otherwise transformed in order to facilitate further processing. As a next step 803, the preprocessed data may be passed to quantizer 112 which quantizes the data. The next step 804, comprises compressing the quantized SAR data using a compression algorithm known to those with skill in the art. In an embodiment, the compression algorithm may comprise HEVC encoding for both compression and decompression of SAR data. As a last step 805, the compressed data may be compacted. The compaction may be a lossless compaction technique, such as those described with reference to FIGS. 4-7. The output of method 800 is a compressed, compacted bit stream of SAR image data which can be stored in a database, requiring much less storage space than would be required to store the original, raw SAR image. The compressed and compacted bit stream may be transmitted to an endpoint for storage or processing. Transmission of the compressed and compacted data require less bandwidth and computing resources than transmitting raw SAR image data.

Figure 9:
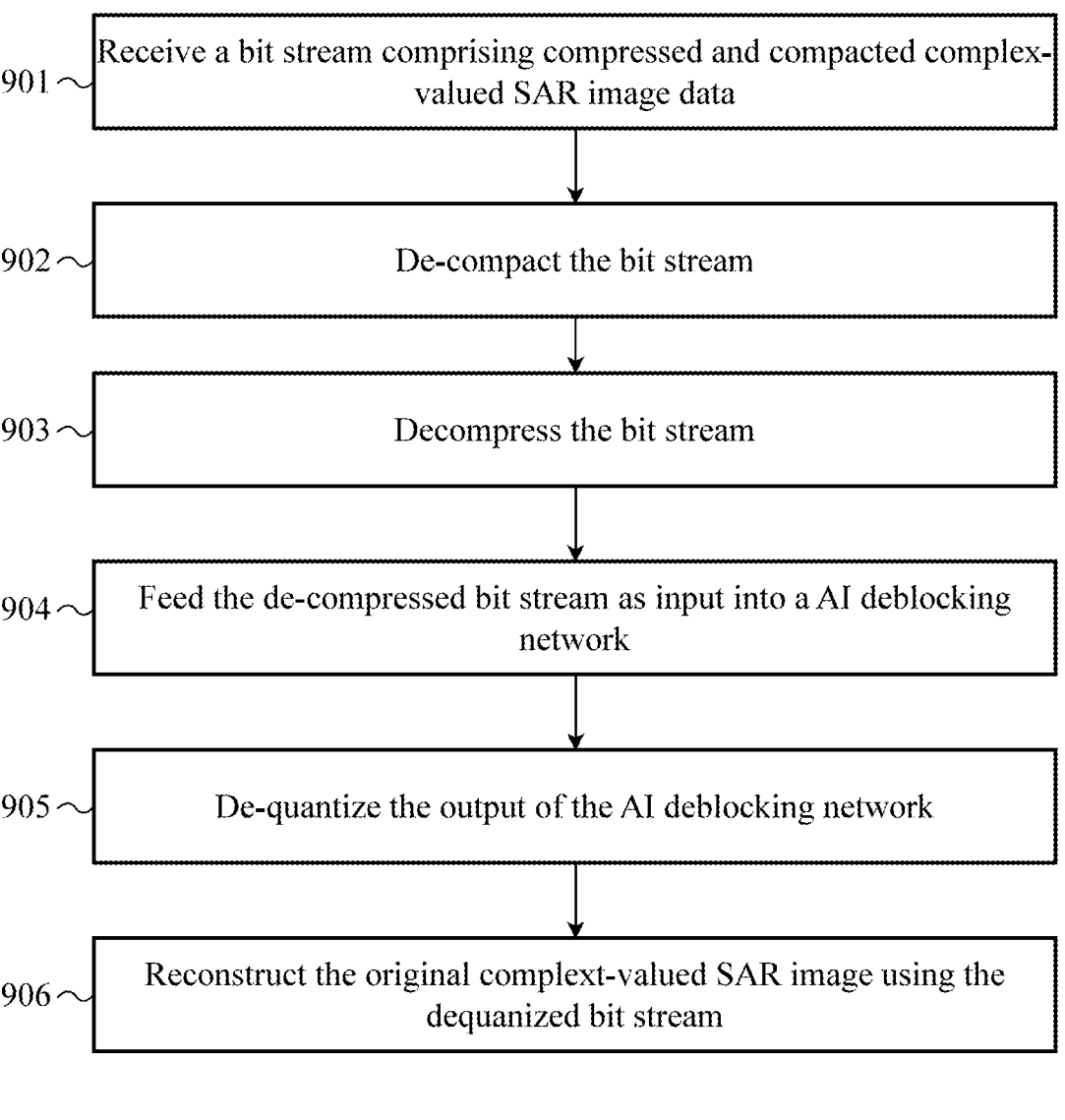
FIG. 9 is a flow diagram illustrating and exemplary method for decompression of a complex-valued SAR image, according to an embodiment.

FIG. 9 is a flow diagram illustrating and exemplary method 900 for decompression of a complex-valued SAR image, according to an embodiment. According to the embodiment, the process begins at step 901 when decoder 120 receives a bit stream comprising compressed and compacted complex-valued SAR image data. The compressed bit stream may be received from encoder 110 or from a suitable data storage device. At step 902, the received bit stream is first de-compacted to produce an encoded (compressed) bit stream. In some embodiments, data reconstruction engine 601 may be implemented as a system for de-compacting a received bit stream. The next step 903, comprising decompressing the de-compacted bit stream using a suitable compression algorithm known to those with skill in the art, such as HEVC encoding. At step 904, the de-compressed SAR data may be fed as input into AI deblocking network 123 for image enhancement via a trained deep learning network. The AI deblocking network may utilize a series of convolutional layers and/or Res-Blocks to process the input data and perform artifact removal on the de-compressed SAR image data. AI deblocking network may be further configured to implement an attention mechanism for the model to capture dependencies between elements regardless of their positional distance. In an embodiment, during training of AI deblocking network, the amplitude loss in conjunction with the SAR loss may be computed and accounted for, further boosting the compression performance of system 100. The output of AI deblocking network 123 can be sent to a quantizer 124 which can execute step 905 by de-quantizing the output bit stream from AI deblocking network. As a last step 906, system can reconstruct the original complex-valued SAR image using the de-quantized bit stream.

FIG. 10 is a flow diagram illustrating an exemplary method for deblocking using a trained deep learning algorithm, according to an embodiment. According to the embodiment, the process begins at step 1001 wherein the trained deep learning algorithm (i.e., AI deblocking network 123) receives a decompressed bit stream comprising SAR I/Q image data. At step 1002, the bit stream is split into a pixel domain and a frequency domain. Each domain may pass through AI deblocking network, but have separate, almost similar processing paths. As a next step 1003, each domain is processed through its respective branch, the branch comprising a series of convolutional layers and ResBlocks. In some implementations, frequency domain may be further processed by a transpose convolution layer. The two branches are combined and used as input for a multi-channel transformer with attention mechanism at step 1004. Multi-channel transformer 300 may perform functions such as downsampling, positional embedding, and various transformations, according to some embodiments. Multi-channel transformer 300 may comprise one or more of the following components: channel-wise attention, transformer self-attention, and/or feedforward layers. In an implementation, the downsampling may be performed via average pooling. As a next step 1005, the AI deblocking network processes the output of the channel-wise transformer. The processing may include the steps of passing the output through one or more convolutional or PRELU layers and/or upsampling the output. As a last step 1006, the processed output may be forwarded to quantizer 124 or some other endpoint for storage or further processing.

Figure 11A:
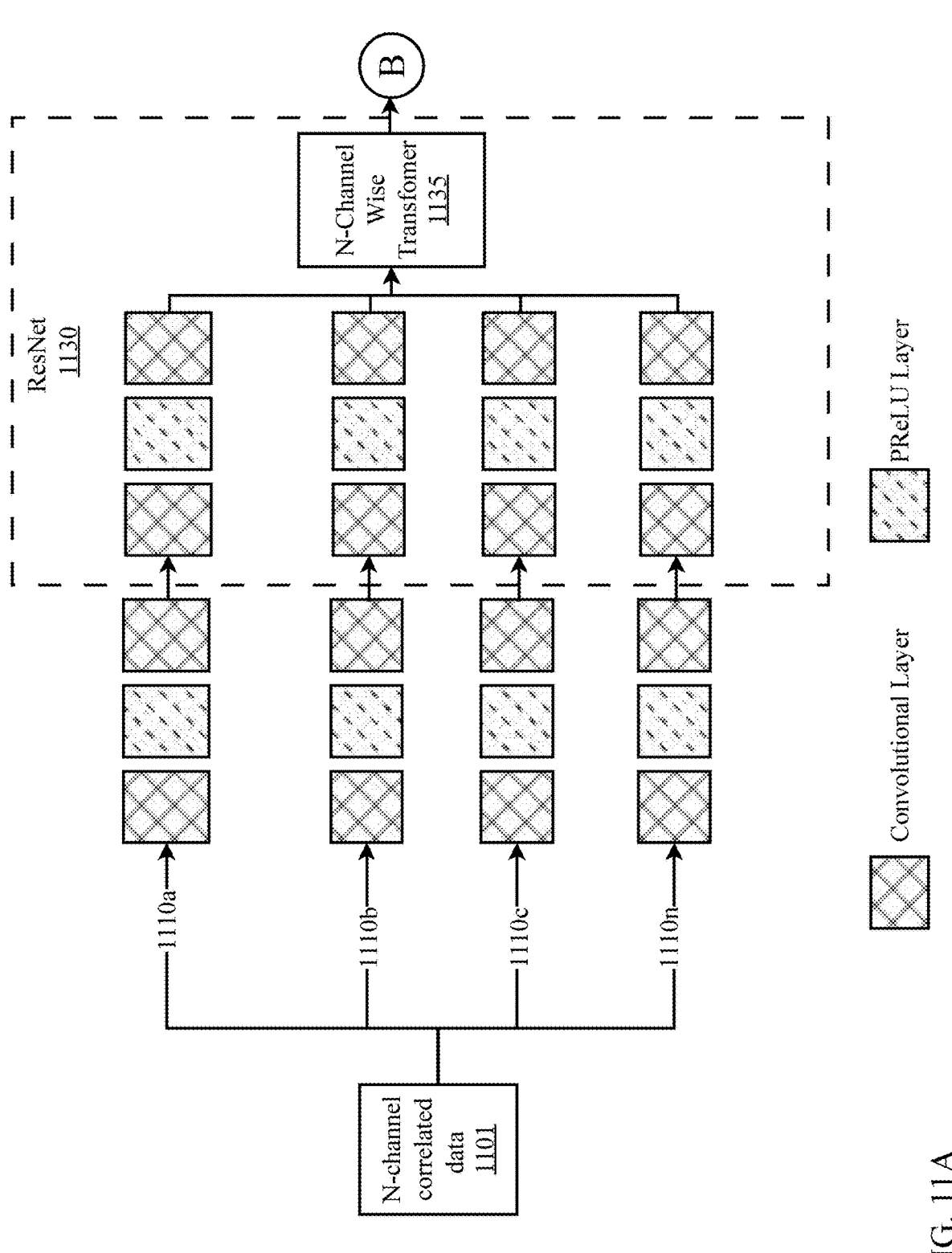
FIGS. 11A and 11B illustrate an exemplary architecture for an AI deblocking network configured to provide deblocking for a general N-channel data stream, according to an embodiment.
Figure 11B:
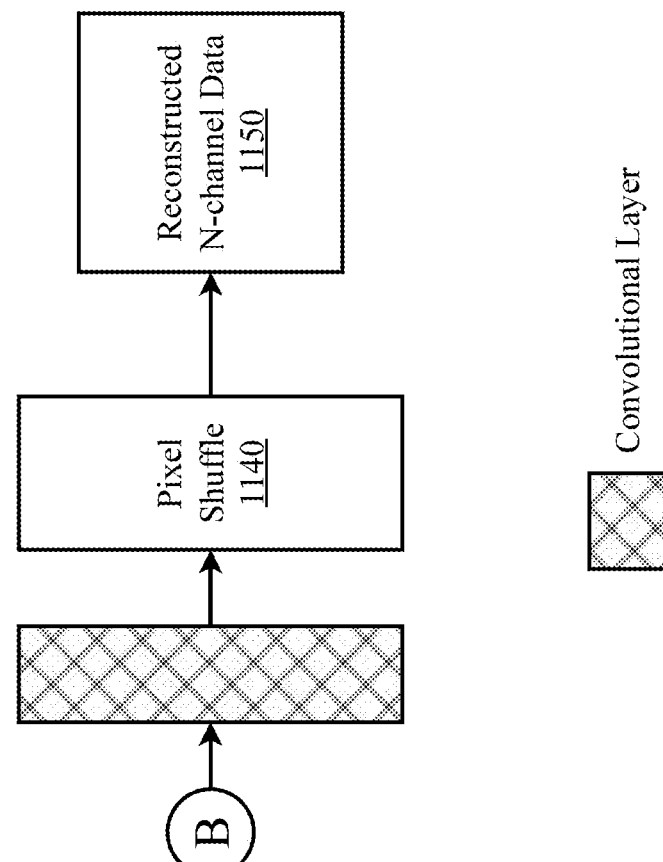

FIGS. 11A and 11B illustrate an exemplary architecture for an AI deblocking network configured to provide deblocking for a general N-channel data stream, according to an embodiment. The term "N-channel" refers to data that is composed of multiple distinct channels of modalities, where each channel represents a different aspect of type of information. These channels can exist in various forms, such as sensor readings, image color channels, or data streams, and they are often used together to provide a more comprehensive understanding of the underlying phenomenon. Examples of N-channel data include, but is not limited to, RGB images (e.g., in digital images, the red, green, and blue channels represent different color information; combining these channels allows for the representation of a wide range of colors), medical imaging (e.g., may include Magnetic Resonance Imaging scans with multiple channels representing different tissue properties, or Computed Tomography scans with channels for various types of X-ray attenuation), audio data (e.g., stereo or multi-channel audio recordings where each channel corresponds to a different microphone or audio source), radar and lidar (e.g., in autonomous vehicles, radar and lidar sensors provide multi-channel data, with each channel capturing information about objects' positions, distances, and reflectivity) SAR image data, text data (e.g., in natural language processing, N-channel data might involve multiple sources of text, such as social media posts and news articles, each treated as a separate channel to capture different textual contexts), sensor networks (e.g., environmental monitoring systems often employ sensor networks with multiple sensors measuring various parameters like temperature, humidity, air quality, and more. Each sensor represents a channel), climate data, financial data, and social network data.

The disclosed AI deblocking network may be trained to process any type of N-channel data, if the N-channel data has a degree of correlation. More correlation between and among the multiple channels yields a more robust and accurate AI deblocking network capable of performing high quality compression artifact removal on the N-channel data stream. A high degree of correlation implies a strong relationship between channels. Using SAR image data has been used herein as an exemplary use case for an AI deblocking network for a N-channel data stream comprising 2 channels, the In-phase and Quadrature components (i.e., I and Q, respectively).

Exemplary data correlations that can be exploited in various implementations of AI deblocking network can include, but are not limited to, spatial correlation, temporal correlation, cross-sectional correlation (e.g., This occurs when different variables measured at the same point in time are related to each other), longitudinal correlation, categorical correlation, rank correlation, time-space correlation, functional correlation, and frequency domain correlation, to name a few.

As shown, an N-channel AI deblocking network may comprise a plurality of branches 1110a-n. The number of branches is determined by the number of channels associated with the data stream. Each branch may initially be processed by a series of convolutional and PRELU layers. Each branch may be processed by resnet 1130 wherein each branch is combined back into a single data stream before being input to N-channel wise transformer 1135, which may be a specific configuration of transformer 300. The output of N-channel wise transformer 1135 may be sent through a final convolutional layer before passing through a last pixel shuffle layer 1140. The output of AI deblocking network for N-channel video/image data is the reconstructed N-channel data 1150.

As an exemplary use case, video/image data may be processed as a 3-channel data stream comprising Green (G), Red (R), and Blue (B) channels. An AI deblocking network may be trained that provides compression artifact removal of video/image data. Such a network would comprise 3 branches, wherein each branch is configured to process one of the three channels (R, G, or B). For example, branch 1110a may correspond to the R-channel, branch 1110b to the G-channel, and branch 1110c to the B-channel. Each of these channels may be processed separately via their respective branches before being combined back together inside resnet 1130 prior to being processed by N-channel wise transformer 1135.

As another exemplary use case, a sensor network comprising a half dozen sensors may be processed as a 6-channel data stream. The exemplary sensor network may include various types of sensors collecting different types of, but still correlated, data. For example, sensor network can include a pressure sensor, a thermal sensor, a barometer, a wind speed sensor, a humidity sensor, and an air quality sensor. These sensors may be correlated to one another in at least one way. For example, the six sensors in the sensor network may be correlated both temporally and spatially, wherein each sensor provides a time series data stream which can be processed by one of the 6 channels 1110a-n of AI deblocking network. As long as AI deblocking network is trained on N-channel data with a high degree of correlation and which is representative of the N-channel data it will encounter during model deployment, it can reconstruct the original data using the methods described herein.

Figure 12:
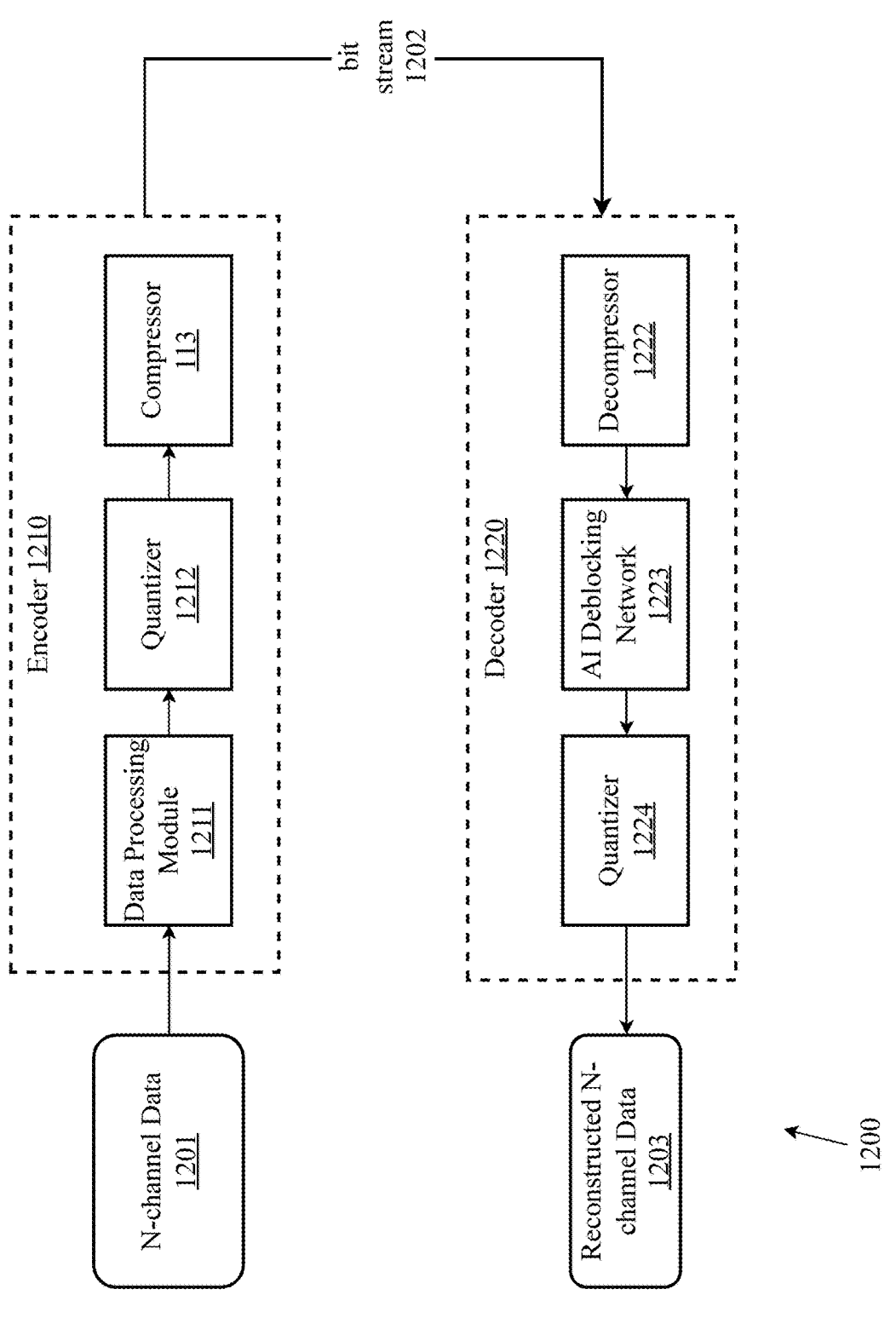
FIG. 12 is a block diagram illustrating an exemplary system architecture for N-channel data compression with predictive recovery, according to an embodiment.

FIG. 12 is a block diagram illustrating an exemplary system architecture 1200 for N-channel data compression with predictive recovery, according to an embodiment. According to the embodiment, the system 1200 comprises an encoder module 1210 configured to receive as input N-channel data 1201 and compress and compact the input data into a bitstream 102, and a decoder module 120 configured to receive and decompress the bitstream 1202 to output a reconstructed N-channel data 1203.

A data processor module 1211 may be present and configured to apply one or more data processing techniques to the raw input data to prepare the data for further processing by encoder 1210. Data processing techniques can include (but are not limited to) any one or more of data cleaning, data transformation, encoding, dimensionality reduction, data slitting, and/or the like.

After data processing, a quantizer 1212 performs uniform quantization on the n-number of channels. Quantization is a process used in various fields, including signal processing, data compression, and digital image processing, to represent continuous or analog data using a discrete set of values. It involves mapping a range of values to a smaller set of discrete values. Quantization is commonly employed to reduce the storage requirements or computational complexity of digital data while maintaining an acceptable level of fidelity or accuracy. Compressor 1213 may be configured to perform data compression on quantized N-channel data using a suitable conventional compression algorithm.

The resulting encoded bitstream may then be (optionally) input into a lossless compactor (not shown) which can apply data compaction techniques on the received encoded bitstream. An exemplary lossless data compaction system which may be integrated in an embodiment of system 1200 is illustrated with reference to FIG. 4-7. For example, lossless compactor may utilize an embodiment of data deconstruction engine 501 and library manager 403 to perform data compaction on the encoded bitstream. The output of the compactor is a compacted bitstream 1202 which can be stored in a database, requiring much less space than would have been necessary to store the raw N-channel data, or it can be transmitted to some other endpoint.

At the endpoint which receives the transmitted compacted bitstream 1202 may be decoder module 1220 configured to restore the compacted data into the original SAR image by essentially reversing the process conducted at encoder module 1210. The received bitstream may first be (optionally) passed through a lossless compactor which de-compacts the data into an encoded bitstream. In an embodiment, a data reconstruction engine 601 may be implemented to restore the compacted bitstream into its encoded format. The encoded bitstream may flow from compactor to decompressor 1222 wherein a data compaction technique may be used to decompress the encoded bitstream into the I/Q channels. It should be appreciated that lossless compactor components are optional components of the system, and may or may not be present in the system, dependent upon the embodiment.

According to the embodiment, an Artificial Intelligence (AI) deblocking network 1223 is present and configured to utilize a trained deep learning network to provide compression artifact removal as part of the decoding process. AI deblocking network 1223 may leverage the relationship demonstrated between the various N-channels of a data stream to enhance the reconstructed N-channel data 1203. Effectively, AI deblocking network 1223 provides an improved and novel method for removing compression artifacts that occur during lossy compression/decompression using a network designed during the training process to simultaneously address the removal of artifacts and maintain fidelity of the original N-channel data signal, ensuring a comprehensive optimization of the network during the training stages.

The output of AI deblocking network 1223 may be dequantized by quantizer 1224, restoring the n-channels to their initial dynamic range. The dequantized n-channel data may be reconstructed and output 1203 by decoder module 1220 or stored in a database.

FIG. 13 is a flow diagram illustrating an exemplary method for processing a compressed n-channel bit stream using an AI deblocking network, according to an embodiment. According to the embodiment, the process begins at step 1301 when a decoder module 1220 receives, retrieves, or otherwise obtains a bit stream comprising n-channel data with a high degree of correlation. At step 1302, the bit stream is split into an n-number of domains. For example, if the received bit stream comprises image data in the form of R-, G,- and B-channels, then the bit stream would be split into 3 domains, one for each color (RGB). At step 1303, each domain is processed through a branch comprising a series of convolutional layers and ResBlocks. The number of layers and composition of said layers may depend upon the embodiment and the n-channel data being processed. At step 1304, the output of each branch is combined back into a single bitstream and used as an input into an n-channel wise transformer 1135. At step 1305, the output of the channel-wise transformer may be processed through one or more convolutional layers and/or transformation layers, according to various implementations. At step 1306, the processed output may be sent to a quantizer for upscaling and other data processing tasks. As a last step 1307, the bit stream may be reconstructed into its original uncompressed form.

Figure 14:
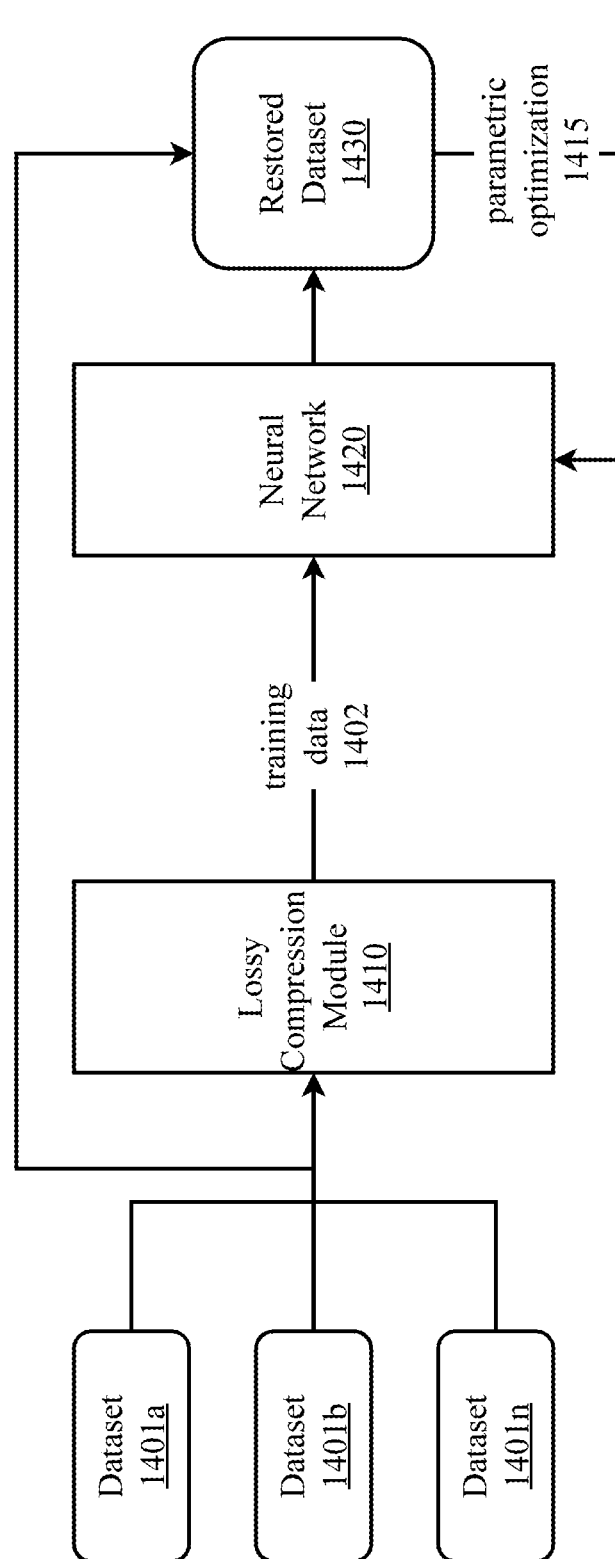
FIG. 14 is a block diagram illustrating a system for training a neural network to perform upsampling of decompressed data after lossy compression, according to an embodiment.

FIG. 14 is a block diagram illustrating a system for training a neural network to perform upsampling of decompressed data after lossy compression, according to an embodiment. The neural network may be referred to herein as a neural upsampler. According to the embodiment, a neural upsampler 1430 may be trained by taking training data 1402 which may comprise sets of two or more correlated datasets 101*a-n* and performing whatever processing that is done to compress the data. This processing is dependent upon the type of data and may be different in various embodiments of the disclosed system and methods. For example, in the SAR imagery use case, the processing and lossy compression steps used quantization and HEVC compression of the I and Q images. The sets of compressed data may be used as input training data 1402 into the neural network 1420 wherein the target output is the original uncompressed data. Because there is correlation between the two or more datasets, the neural upsampler learns how to restore "lost" data by leveraging the cross-correlations.

For each type of input data, there may be different compression techniques used, and different data conditioning for feeding into the neural upsampler. For example, if the input datasets 101*a-n* comprise a half dozen correlated time series from six sensors arranged on a machine, then delta encoding or a swinging door algorithm may be implemented for data compression and processing.

The neural network 1420 may process the training data 1402 to generate model training output in the form of restored dataset 1430. The neural network output may be compared against the original dataset to check the model's precision and performance. If the model output does not satisfy a given criteria or some performance threshold, then parametric optimization 1415 may occur wherein the training parameters and/or network hyperparameters may be updated and applied to the next round of neural network training.

FIG. 15 is a flow diagram illustrating an exemplary method 1500 for training a neural network to perform upsampling of decompressed data after lossy compression, according to an embodiment. According to an embodiment, the process begins at step 1501 by creating a training dataset comprising compressed data by performing lossy compression on two or more datasets which are substantially correlated. As a next step 1502, the training dataset is used to train a neural network (i.e., neural upsampler) configured to leverage the correlation between the two or more datasets to generate as output a reconstructed dataset. At step 1503, the output of the neural network is compared to the original two more datasets to determine if the performance of the neural network at reconstructing the compressed data. If the model performance is not satisfactory, which may be determined by a set of criteria or some performance metric or threshold, then the neural network model parameters and/or hyperparameters may be updated 1504 and applied to the next round of training as the process moves to step 1502 and iterates through the method again.

Figure 16:
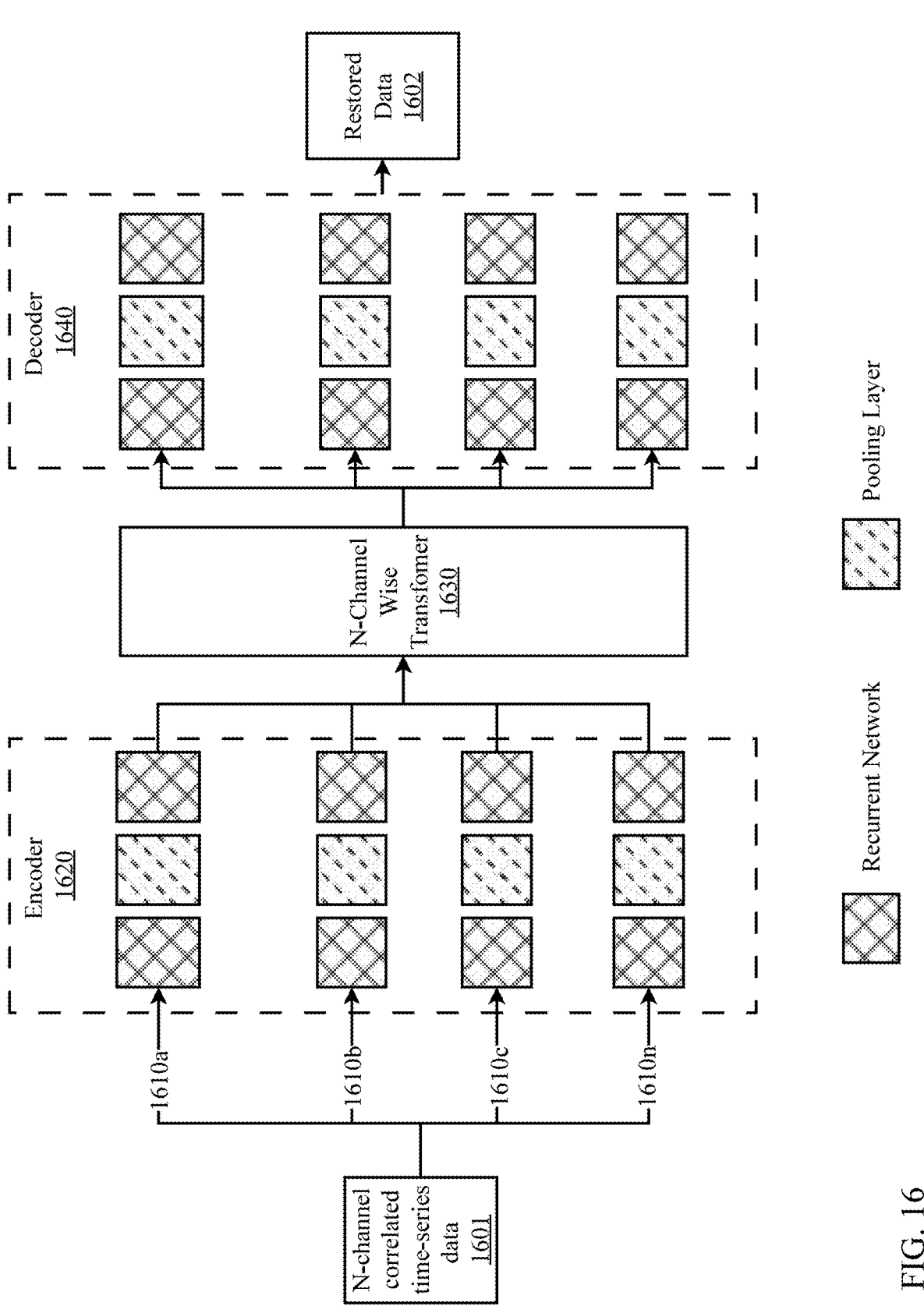
FIG. 16 is a block diagram illustrating an exemplary architecture for a neural upsampler configured to process N-channel time-series data, according to an embodiment.

FIG. 16 is a block diagram illustrating an exemplary architecture for a neural upsampler configured to process N-channel time-series data, according to an embodiment. The neural upsampler may comprise a trained deep learning algorithm. According to the embodiment, a neural upsampler configured to process time-series data may comprise a recurrent autoencoder with an n-channel transformer attention network. In such an embodiment, the neural upsampler may be trained to process decompressed time-series data wherein the output of the upsampler is restored time-series data (i.e., restore most of the lost data due to the lossy compression). The upsampler may receive decompressed n-channel time-series data comprising two or more data sets of time-series data which are substantially correlated. For example, the two or more data sets may comprise multiple sets of Internet of Things (IoT) sensor data from sensors that are likely to be temporally correlated. For instance, consider a large number of sensors on a single complex machine (e.g., a combine tractor, a 3D printer, construction equipment, etc.) or a large number of sensors in a complex system such as a pipeline or refinery.

The n-channel time-series data may be received split into separate channels 1610*a-n* to be processed individually by encoder 1620. In some embodiments, encoder 1620 may employ a series of various data processing layers which may comprise recurrent neural network (RNN) layers, pooling layers, PRELU layers, and/or the like. In some implementations, one or more of the RNN layers may comprise a Long Short-Term Memory (LSTM) network. In some implementations, one or more of the RNN layers may comprise a sequence-to-sequence model. In yet another implementation, the one or more RNN layer may comprise a gate recurrent unit (GRU). Each channel may be processed by its own series of network layers wherein the encoder 1620 can learn a representation of the input data which can be used to determine the defining features of the input data. Each individual channel then feeds into an n-channel wise transformer 1630 which can learn the interdependencies between the two or more channels of correlated time-series data. The output of the n-channel wise transformer 1630 is fed into the decoder 1640 component of the recurrent autoencoder in order to restore missing data lost due to a lossy compression implemented on the time-series data. N-channel wise transformer 1630 is designed so that it can weigh the importance of different parts of the input data and then capture long-range dependencies between and among the input data. The decoder may process the output of the n-channel wise transformer 1630 into separate channels comprising various layers as described above. The output of decoder 1640 is the restored time-series data 1602, wherein most of the data which was "lost" during lossy compression can be recovered using the neural upsampler which leverages the interdependencies hidden within correlated datasets.

In addition to RNNs and their variants, other neural network architectures like CNNs and hybrid models that combine CNNs and RNNs can also be implemented for processing time series and sensor data, particularly when dealing with sensor data that can be structured as images or spectrograms. For example, if you had, say, 128 time series streams, it could be structured as two 64×64 pixel images (64 times series each, each with 64 time steps), and then use the same approach as the described above with respect to the SAR image use case. In an embodiment, a one-dimensional CNN can be used as a data processing layer in encoder 1620 and/or decoder 1640. The selection of the neural network architecture for time series data processing may be based on various factors including, but not limited to, the length of the input sequences, the frequency and regularity of the data points, the need to handle multivariate input data, the presence of exogenous variables or covariates, the computational resources available, and/or the like.

The exemplary time-series neural upsampler described in FIG. 16 may be trained on a training dataset comprising a plurality of compressed time-series data sourced from two or more datasets which are substantially correlated. For example, in a use case directed towards neural upsampling of IoT sensor data, the neural upsampler may be trained on a dataset comprising compressed IoT sensor data. During training, the output of the neural upsampler may be compared against the non-compressed version of the IoT sensor data to determine the neural upsampler's performance on restoring lost information.

Figure 17:
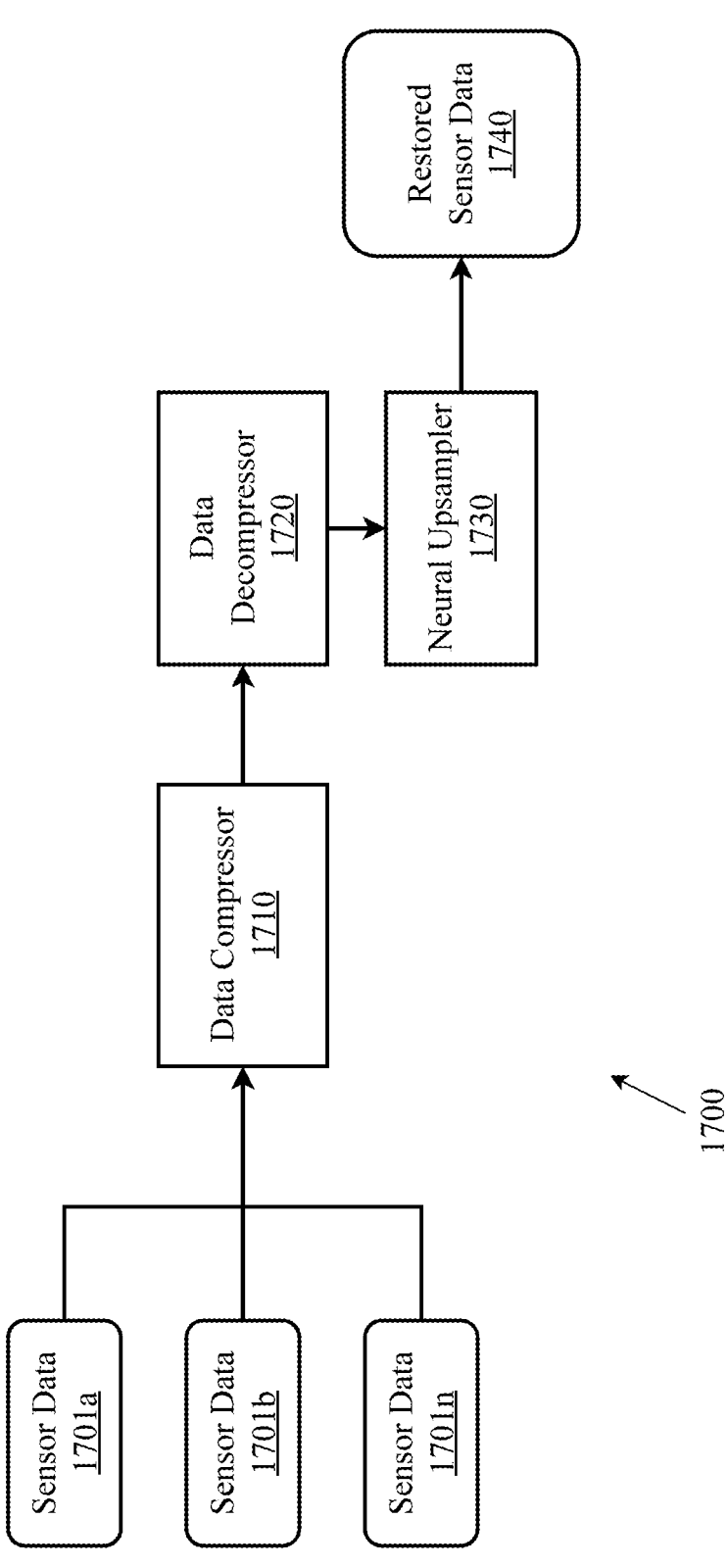
FIG. 17 is a block diagram illustrating an exemplary system architecture for upsampling of decompressed sensor data after lossy compression using a neural network, according to an embodiment.

FIG. 17 is a block diagram illustrating an exemplary system architecture 1700 for upsampling of decompressed sensor data after lossy compression using a neural network, according to an embodiment. According to the embodiment, a neural upsampler 1730 is present and configured to receive decompressed sensor data (e.g., time-series data obtained from an IoT device) and restore the decompressed data by leveraging learned data correlations and inter- and intra-dependencies. According to an embodiment, the system may receive a plurality of sensor data 1701a-n from two or more sensors/devices, wherein the sensor data are substantially correlated. In an embodiment, the plurality of sensor data 1701a-n comprises time-series data. Time-series data received from two or more sensors may be temporally correlated, for example, IoT data from a personal fitness device and a blood glucose monitoring device during the time when a user of both devices is exercising may be correlated in time and by heart rate. As another example, a large number of sensors used to monitor a manufacturing facility may be correlated temporally.

A data compressor 1710 is present and configured to utilize one or more data compression methods on received sensor data 1701a-n. The data compression method chosen must be a lossy compression method. Exemplary types of lossy compression that may be used in some embodiments may be directed towards image or audio compression such as JPEG and MP3, respectively. For time series data lossy compression methods that may be implemented include (but is not limited to) one or more of the following: delta encoding, swinging door algorithm, batching, data aggregation, feature extraction. In an implementation, data compressor 1710 may implement network protocols specific for IoT such as message queuing telemetry transport (MQTT) for supporting message compression on the application layer and/or constrained application protocol (CoAP) which supports constrained nodes and networks and can be used with compression.

The compressed multi-channel sensor data 1701a-n may be decompressed by a data decompressor 1720 which can utilize one or more data decompression methods known to those with skill in the art. The output of data decompressor 1720 is a sensor data stream(s) of decompressed data which is missing information due to the lossy nature of the compression/decompression methods used. The decompressed sensor data stream(s) may be passed to neural upsampler 1730 which can utilize a trained neural network to restore most of the "lost" information associated with the decompressed sensor data stream(s) by leveraging the learned correlation(s) between and among the various sensor data streams. The output of neural upsampler 1730 is restored sensor data 1740.

Figure 18:
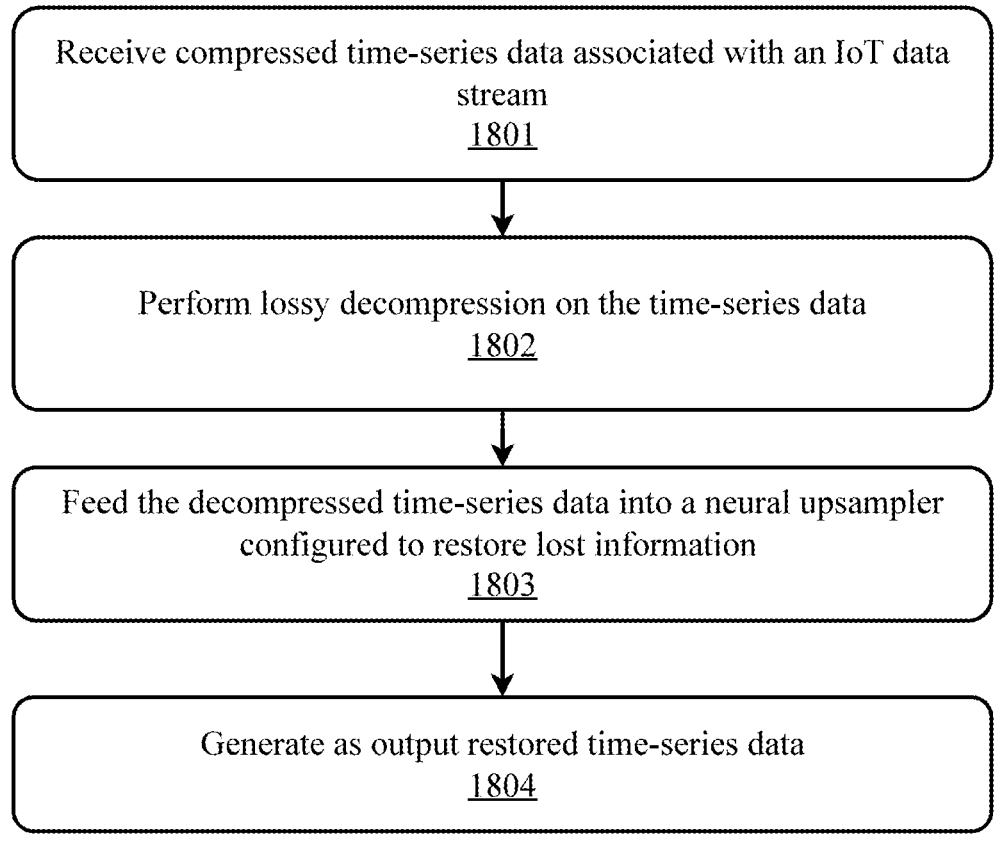
FIG. 18 is a flow diagram illustrating an exemplary method for performing neural upsampling of two or more time-series data streams, according to an embodiment.

FIG. 18 is a flow diagram illustrating an exemplary method 1800 for performing neural upsampling of two or more time-series data streams, according to an embodiment. In this example, the two or more time-series streams may be associated with large sets of IoT sensors/devices. The two or more time-series streams are substantially correlated. The two or more time-series data streams may be temporally correlated. For example, a plurality of IoT sensors may be time-synchronized to better understand cause-and-effect relationships.

A neural upsampler which has been trained on compressed time-series data associated with one or more IoT sensor channels is present and configured to restore time-series data which has undergone lossy data compression and decompression by leveraging the correlation between the sensor data streams. A non-exhaustive list of time-series data correlations that may be used by an embodiment of the system and method can include cross-correlation and auto-correlation.

The two or more time-series data streams may be processed by a data compressor 1710 employing a lossy compression method. The lossy compression method may implement a lossy compression algorithm appropriate for compressing time-series data. The choice of compression implementation may be based on various factors including, but not limited to, the type of data being processed, the computational resources and time required, and the use case of the upsampler. Exemplary time-series data compression techniques which may be used include, but are not limited to, delta encoding, swinging door algorithm data aggregation, feature extraction, and batching, to name a few. The compressed time series data may be store in a database and/or transmitted to an endpoint. The compressed time-series data may be sent to a data decompressor 1720 which may employ a lossy decompression technique on the compressed time-series data. The decompressed data may be sent to the neural upsampler which can restore the decompressed data to nearly its original state by leveraging the temporal (and/or other) correlation between the time-series IoT sensor data streams. The compressed time-series data is received by data decompressor 1720 at step 1801. At data decompressor 1720 the compressed time-series data may be decompressed via a lossy decompression algorithm at step 1802.

A neural upsampler for restoration of time-series (e.g., IoT sensor data) data received from two or more data channels may be trained using two or more datasets comprising compressed time-series data which is substantially correlated. For example, the two or more datasets may comprise time-series data from a plurality of sensors affixed to a long-haul semi-truck and configured to monitor various aspects of the vehicles operation and maintenance and report the monitored data to a central data processing unit which can compress and transmit the data for storage or further processing. The two or more sensor channels are correlated in various ways such as temporally. In various embodiments, each channel of the received time-series data may be fed into its own neural network comprising a series of convolutional and/or recurrent and ReLU and/or pooling layers which can be used to learn latent correlations in the feature space that can be used to restore data which has undergone lossy compression. A multi-channel transformer may be configured to receive the output of each of the neural networks produce, learn from the latent correlation in the feature space, and produce reconstructed time-series data. At step 1803, the decompressed time-series data may be used as input to the trained neural upsampler configured to restore the lost information of the decompressed time-series data. The neural upsampler can process the decompressed data to generate as output restored time-series data at step 1804.

Figure 19:
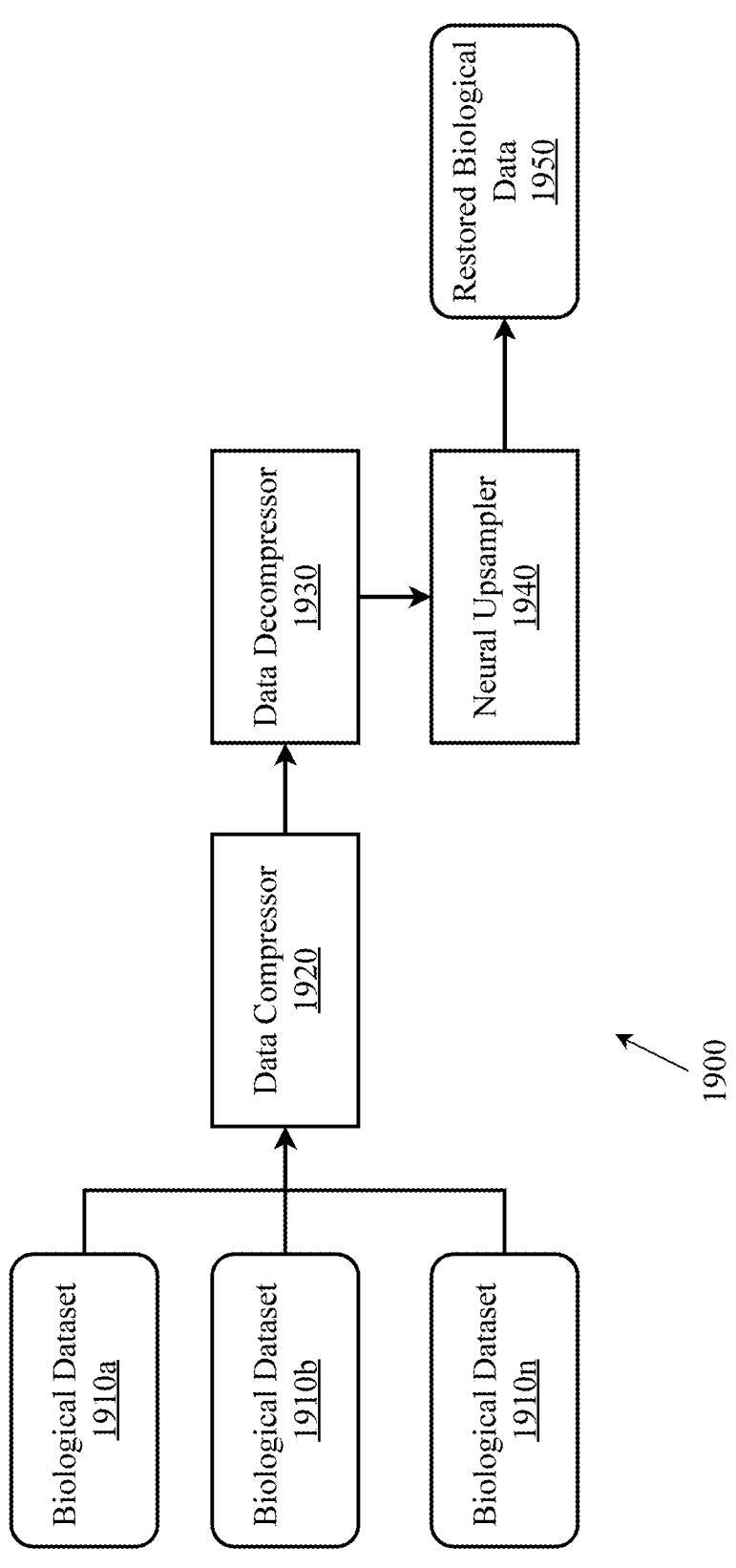
FIG. 19 is a block diagram illustrating an exemplary system architecture for neural upsampling of two or more genomic datasets, according to an embodiment.

FIG. 19 is a block diagram illustrating an exemplary system architecture for neural upsampling of two or more biological datasets, according to an embodiment. Biological data 1910*a-n* may comprise, for example, any one or more of DNA sequences, single nucleotide polymorphisms (SNPs) gene expression data, epigenetic data, structural biological data, mitochondrial DNA sequences, and/or the like. These examples highlight different layers of biological information, from the basic DNA sequence to variations, gene expression, and epigenetic modifications. Analyzing and integrating multiple types of biological data are crucial for a comprehensive understanding of biological processes, evolution, and the genetic basis of diseases. Thus, it would be beneficial to have a system, method, and/or computer readable instructions capable of providing neural upsampling of biological data (e.g., human genomes or subsets of them, any parallel genome data sets, two or more persons mitochondrial DNA sequences, etc.) which has undergone lossy compression, therefore nearly restoring all the lost data.

In an embodiment, biological data 1910*a-n* may comprise parallel genome datasets. Parallel genome datasets typically refer to multiple sets of genomic data that are generated or analyzed simultaneously. Using parallel sequencing runs, multiple samples may undergo DNA sequencing simultaneously in parallel, generating multiple sets of sequencing data concurrently. For example, in a genomics laboratory, several DNA samples might be processed and sequenced using high-throughput sequencing technologies in a single sequencing run, producing parallel datasets. In another example, genomic data from different individuals or populations may be collected and analyzed concurrently to study genetic diversity, population structure, and evolutionary patterns. Researchers might analyze genome sequences from individuals of different ethnicities or geographic regions in parallel to investigate population-specific genetic variations.

There are several common data formats used for storing and transmitting biological data, and which may be used in various implementations of the disclosed system and methods. These formats are designed to efficiently represent the vast amount of information generated through various genomic technologies. One such format of biological data which may be processed by system 1900 is Format for Sequence Data (FASTA). FASTA is a text-based format for representing nucleotide or protein sequences. It consists of a header line starting with ">", followed by the sequence data. This format may be used when processing genomic data such as DNA, RNA, and protein sequences. Similarly, Format for Quality Scores (FASTQ) may be used in some implementations. FASTQ is a text-based format that extends FASTA by including quality scores for each base in the sequence. It is commonly used for storing data from next-generation sequencing (NGS) platforms.

Another exemplary format which may be processed by system 1900 is sequence alignment/mapping (SAM/BAM). SAM is a text-based format for representing sequence alignment data, while BAM is the binary equivalent. SAM/BAM files store aligned sequencing reads along with quality scores, mapping positions, and other relevant information. SAM/BAM may be implemented in use cases for storing and exchanging data related to sequence alignments, such as is the case in the context of NGS data. As a final example, variant call format (VCF) may be implemented in some embodiments of system 1900. VCF is a text-based format for representing genomic variations, such as single nucleotide polymorphisms (SNPs), insertions, deletions, and structural variants.

The biological data may be received at a data compressor 1920 which is present and configured to utilize one or more data compression methods on received genomic data 1910*a-n*. Biological data, especially raw sequencing data, can be massive, and compression techniques are often employed to reduce storage requirements and facilitate data transfer. The data compression method chosen must be a lossy compression method. Exemplary types of lossy compression that may be used in some embodiments include quality score quantization, reference-based compression, subsampling, biological data transformation, and lossy compression of read data.

In an embodiment where quality score quantization is implemented, quality scores associated with each base in sequencing data represent the confidence in the accuracy of the base call. These scores are often encoded with high precision, but for compression purposes, they can be quantized to reduce the bit depth, introducing a level of information loss. Higher quantization levels reduce the precision of quality scores but can significantly reduce file sizes.

In an embodiment, where reference-based compression is implemented, only the differences between the reference biological data and the sample data is stored. As an example, instead of storing the entire genomic sequence, some compression methods store only the differences between the target sequence and a reference genome. Variations and mutations are encoded, while the reference genome provides a framework. This method can achieve substantial compression, but some specific information about the individual's genome is lost. Raw read data from sequencing platforms may contain redundant or noisy information. Lossy compression algorithms may filter or smooth the data to reduce redundancy or noise. While this can result in higher compression, it may lead to the loss of some information, especially in regions with lower sequencing quality.

Biological data compressed by data compressor 1920 may then be sent to a data decompressor 1930 which can utilize one or more data decompression methods known to those with skill in the art. The output of data decompressor 1930 is a biological data stream(s) of decompressed data which is missing information due to the lossy nature of the compression/decompression methods used. The decompressed biological data stream(s) may be passed to neural upsampler 1940 which can utilize a trained neural network to restore most of the "lost" information associated with the decompressed biological data stream(s) by leveraging the learned correlation(s) between and among the various biological datasets. The output of neural upsampler 1940 is restored biological data 1950.

According to various embodiments, system 1900 utilizes a trained neural upsampler to leverage correlations in the received two or more genomic datasets 1910*a-n* in order to restore lost data. In an implementations, neural upsampler 1940 may comprise a series of recurrent neural network layers, pooling layers, an n-channel transformer, and/or convolutional layers as described herein. In an embodiment, neural upsampler 1940 may be trained on a training dataset comprising a corpus of compressed biological data, wherein the compressed biological data is correlated. The neural upsampler may be trained to generate as output biological data, which is at close to its original state, prior to undergoing lossy data compression. The biological data which was used to create the training dataset may be kept and used to validate the training output of neural upsampler, in this way the neural upsampler can be trained to generate output which nearly matches the original, uncompressed biological data.

Biological datasets can be correlated with each other in various ways, providing valuable insights into biological relationships, evolutionary history, and disease associations. There are some ways in which distinct biological datasets can be correlated, and which may be learned and leveraged by a trained neural upsampler 1940 to restore biological data which has been processed via lossy compression/decompression. For example, genetic variation and linkage disequilibrium can provide correlation between and among genetic datasets 1910*a-n*. SNPs are variations at a single nucleotide position in the DNA sequence. Correlating SNP data across different genomic datasets can reveal patterns of genetic variation and linkage disequilibrium. Haplotype blocks found in genomic data may be used as a learned correlation by neural upsampler. Haplotypes are combinations of alleles on a single chromosome. Understanding the correlation of haplotypes across datasets helps in identifying linked genetic variations. Yet another correlation that can be found among genetic datasets is phenotypic correlation. Correlating genomic data with phenotypic information can identify genetic variants associated with specific traits or diseases. This is commonly done through Genome-Wide Association Studies (GWAS) and can involve comparing different genomic datasets.

More examples of genetic data correlations which may be leveraged in one or more embodiments include evolutionary relationships, gene expression correlation, epigenetic correlations, structural genomic correlation, functional annotations, and population genetics. Human mitochondrial DNA (mtDNA) sequences can be correlated to one another in several ways to understand genetic relationships, population structure, and evolutionary history. Some common approaches for analyzing and correlating human mitochondrial sequences can include phylogenetic analysis, haplogroup assignment, and population genetics and diversity measures. Phylogenetic trees are constructed based on sequence differences, revealing the evolutionary relationships among different mitochondrial haplotypes. This is often done using methods like Maximum Likelihood or Bayesian inference. Phylogenetic trees help identify clades, lineages, and common ancestors, providing insights into the historical relationships among mitochondrial sequences. Mitochondrial DNA is categorized into haplogroups, which represent major branches of the mitochondrial phylogenetic tree. Haplogroups are defined by specific polymorphisms and sequence variations. Assigning individuals to haplogroups allows for broader categorization of mtDNA diversity and helps trace maternal lineages. A neural upsampler can use the correlations in genomic datasets to be trained to restore lost data.

Figure 20:
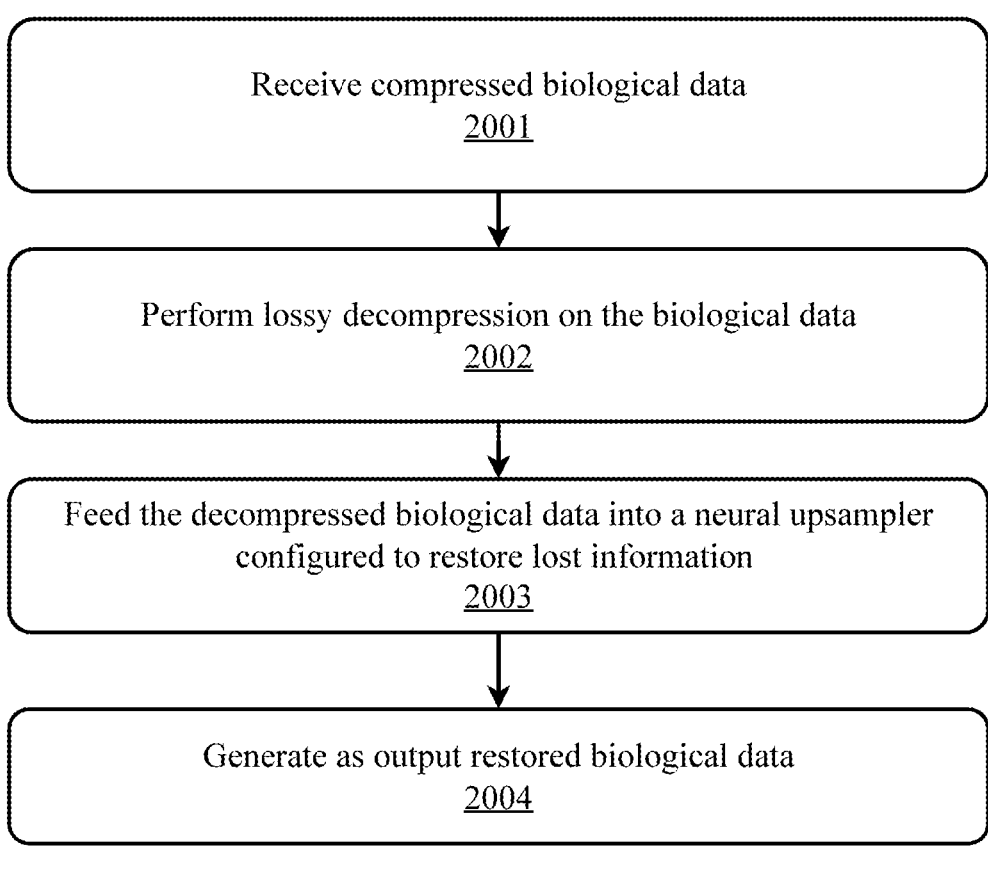
FIG. 20 is a flow diagram illustrating an exemplary method for performing neural upsampling of two or more genomic datasets, according to an embodiment.

FIG. 20 is a flow diagram illustrating an exemplary method 2000 for performing neural upsampling of two or more biological datasets, according to an embodiment. In this example, the two or more biological datasets (also referred to as data streams) may be associated with human genomic data (e.g., human genome). The two or more genomic datasets are substantially correlated as described herein. For example, two or more people's mitochondrial DNA sequences will be closely related.

A neural upsampler which has been trained on compressed biological data is present and configured to restore time-series data which has undergone lossy data compression and decompression by leveraging the correlation between the genomic datasets. A non-exhaustive list of biological data correlations that may be used by an embodiment of the system and method can include genetic variation and linkage disequilibrium, and haplotype blocks.

The two or more biological datasets may be processed by a data compressor 1920 employing a lossy compression method. The lossy compression method may implement a lossy compression algorithm appropriate for compressing biological data. The choice of compression implementation may be based on various factors including, but not limited to, the type of data being processed, the computational resources and time required, and the use case of the upsampler. Exemplary biological data compression techniques which may be used include, but are not limited to, quality score quantization, reference-based compression, subsampling, and biological data transformation, to name a few. The compressed biological data may be stored in a database and/or transmitted to an endpoint. The compressed biological data may be sent to a data decompressor 1930 which may employ a lossy decompression technique on the compressed genomic data. The decompressed data may be sent to the neural upsampler which can restore the decompressed data to nearly its original state by leveraging biological variation (and/or other) correlation between the biological datasets. The compressed biological data is received by data decompressor 1930 at step 2001. At data decompressor 1930 the compressed biological data may be decompressed via a lossy decompression algorithm at step 2002.

A neural upsampler for restoration of genomic (e.g., human genomes or subsets thereof) data received from two or more data channels may be trained using two or more datasets comprising compressed genomic data which is substantially correlated. For example, the two or more datasets may comprise genomic data from a subset of the human genome. Subsets of human genomes refer to specific groups or categories of genetic information within the larger human population. These subsets can be defined based on various criteria, such as geographical origin, shared genetic features, or clinical characteristics. Here are some examples of subsets of human genomes: haplogroups, population specific genomic variation, ancestral populations, ethnic and geographical groups, disease-specific subsets, founder populations (i.e., groups of individuals who established a new population, often with a limited gene pool), isolate populations, age-specific subsets, long-lived individuals, and/or the like. The two or more subsets of human genomes are correlated in various ways such as temporally. In various embodiments, each channel of the received genomic data may be fed into its own neural network comprising a series of convolutional and/or recurrent and ReLU and/or pooling layers which can be used to learn latent correlations in the feature space that can be used to restore data which has undergone lossy compression. A multi-channel transformer may be configured to receive the output that each of the neural networks produce, learn from the latent correlation in the feature space, and produce reconstructed genomic data. At step 2003, the decompressed genomic data may be used as input to the trained neural upsampler configured to restore the lost information of the decompressed genomic data. The neural upsampler can process the decompressed data to generate as output restored genomic data at step 2004.

Exemplary Computing Environment

Figure 21:
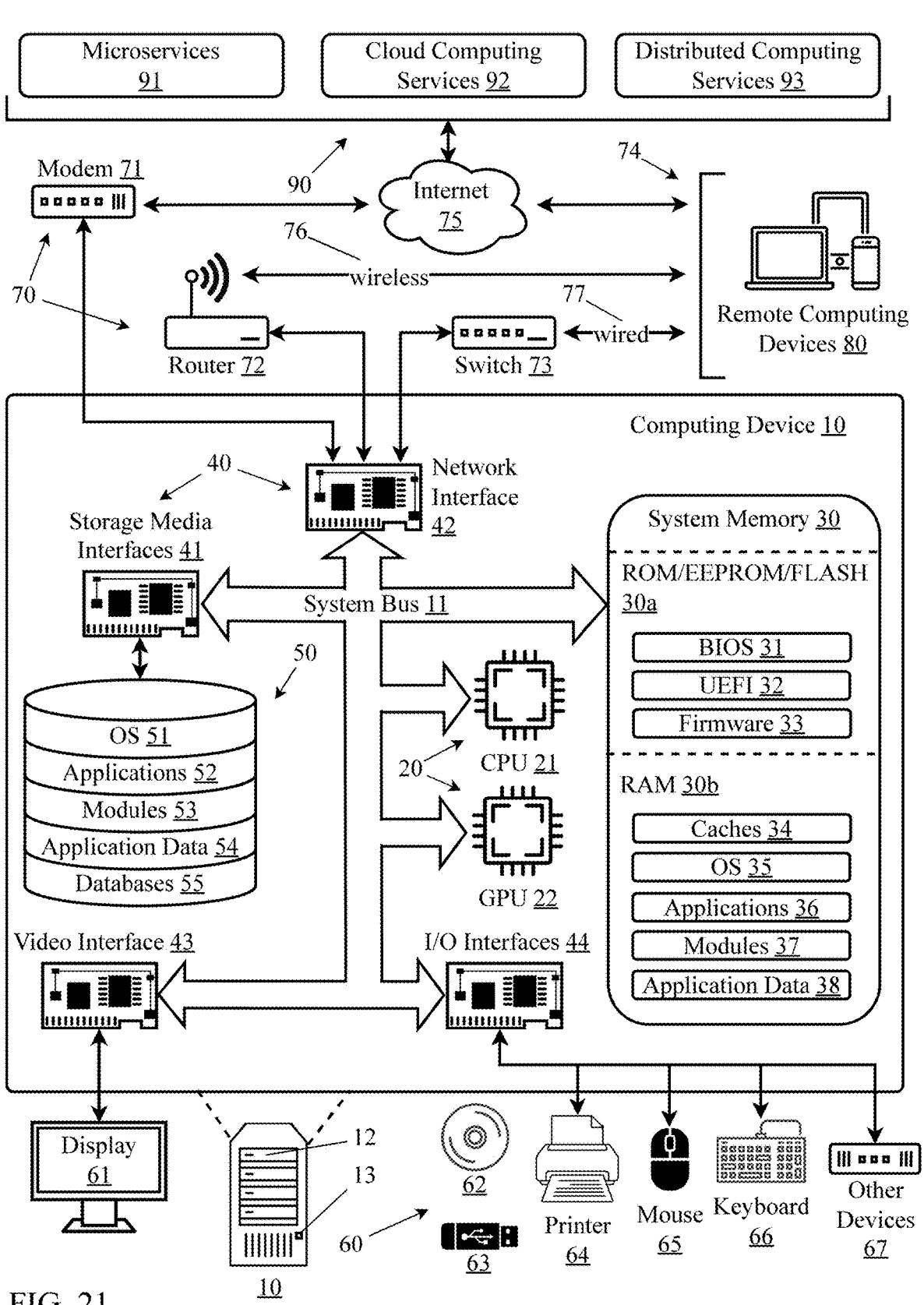
FIG. 21 illustrates an exemplary computing environment on which an embodiment described herein may be implemented, in full or in part.

FIG. 21 illustrates an exemplary computing environment on which an embodiment described herein may be implemented, in full or in part. This exemplary computing environment describes computer-related components and processes supporting enabling disclosure of computer-implemented embodiments. Inclusion in this exemplary computing environment of well-known processes and computer components, if any, is not a suggestion or admission that any embodiment is no more than an aggregation of such processes or components. Rather, implementation of an embodiment using processes and components described in this exemplary computing environment will involve programming or configuration of such processes and components resulting in a machine specially programmed or configured for such implementation. The exemplary computing environment described herein is only one example of such an environment and other configurations of the components and processes are possible, including other relationships between and among components, and/or absence of some processes or components described. Further, the exemplary computing environment described herein is not intended to suggest any limitation as to the scope of use or functionality of any embodiment implemented, in whole or in part, on components or processes described herein.

The exemplary computing environment described herein comprises a computing device 10 (further comprising a system bus 11, one or more processors 20, a system memory 30, one or more interfaces 40, one or more non-volatile data storage devices 50), external peripherals and accessories 60, external communication devices 70, remote computing devices 80, and cloud-based services 90.

System bus 11 couples the various system components, coordinating operation of and data transmission between, those various system components. System bus 11 represents one or more of any type or combination of types of wired or wireless bus structures including, but not limited to, memory busses or memory controllers, point-to-point connections, switching fabrics, peripheral busses, accelerated graphics ports, and local busses using any of a variety of bus architectures. By way of example, such architectures include, but are not limited to, Industry Standard Architecture (ISA) busses, Micro Channel Architecture (MCA) busses, Enhanced ISA (EISA) busses, Video Electronics Standards Association (VESA) local busses, a Peripheral Component Interconnects (PCI) busses also known as a Mezzanine busses, or any selection of, or combination of, such busses. Depending on the specific physical implementation, one or more of the processors 20, system memory 30 and other components of the computing device 10 can be physically co-located or integrated into a single physical component, such as on a single chip. In such a case, some or all of system bus 11 can be electrical pathways within a single chip structure.

Computing device may further comprise externally-accessible data input and storage devices 12 such as compact disc read-only memory (CD-ROM) drives, digital versatile discs (DVD), or other optical disc storage for reading and/or writing optical discs 62; magnetic cassettes, magnetic tape, magnetic disk storage, or other magnetic storage devices; or any other medium which can be used to store the desired content and which can be accessed by the computing device 10. Computing device may further comprise externally-accessible data ports or connections 12 such as serial ports, parallel ports, universal serial bus (USB) ports, and infrared ports and/or transmitter/receivers. Computing device may further comprise hardware for wireless communication with external devices such as IEEE 1394 ("Firewire") interfaces, IEEE 802.11 wireless interfaces, BLUETOOTH® wireless interfaces, and so forth. Such ports and interfaces may be used to connect any number of external peripherals and accessories 60 such as visual displays, monitors, and touch-sensitive screens 61, USB solid state memory data storage drives (commonly known as "flash drives" or "thumb drives") 63, printers 64, pointers and manipulators such as mice 65, keyboards 66, and other devices 67 such as joysticks and gaming pads, touchpads, additional displays and monitors, and external hard drives (whether solid state or disc-based), microphones, speakers, cameras, and optical scanners.

Processors 20 are logic circuitry capable of receiving programming instructions and processing (or executing) those instructions to perform computer operations such as retrieving data, storing data, and performing mathematical calculations. Processors 20 are not limited by the materials from which they are formed, or the processing mechanisms employed therein, but are typically comprised of semiconductor materials into which many transistors are formed together into logic gates on a chip (i.e., an integrated circuit or IC). The term processor includes any device capable of receiving and processing instructions including, but not limited to, processors operating on the basis of quantum computing, optical computing, mechanical computing (e.g., using nanotechnology entities to transfer data), and so forth. Depending on configuration, computing device 10 may comprise more than one processor. For example, computing device 10 may comprise one or more central processing units (CPUs) 21, each of which itself has multiple processors or multiple processing cores, each capable of independently or semi-independently processing programming instructions. Further, computing device 10 may comprise one or more specialized processors such as a graphics processing unit (GPU) 22 configured to accelerate processing of computer graphics and images via a large array of specialized processing cores arranged in parallel.

System memory 30 is processor-accessible data storage in the form of volatile and/or nonvolatile memory. System memory 30 may be either or both of two types: non-volatile memory and volatile memory. Non-volatile memory 30a is not erased when power to the memory is removed, and includes memory types such as read only memory (ROM), electronically-erasable programmable memory (EEPROM), and rewritable solid state memory (commonly known as "flash memory"). Non-volatile memory 30a is typically used for long-term storage of a basic input/output system (BIOS) 31, containing the basic instructions, typically loaded during computer startup, for transfer of information between components within computing device, or a unified extensible firmware interface (UEFI), which is a modern replacement for BIOS that supports larger hard drives, faster boot times, more security features, and provides native support for graphics and mouse cursors. Non-volatile memory 30a may also be used to store firmware comprising a complete operating system 35 and applications 36 for operating computer-controlled devices. The firmware approach is often used for purpose-specific computer-controlled devices such as appliances and Internet-of-Things (IoT) devices where processing power and data storage space is limited. Volatile memory 30b is erased when power to the memory is removed and is typically used for short-term storage of data for processing. Volatile memory 30b includes memory types such as random access memory (RAM), and is normally the primary operating memory into which the operating system 35, applications 36, program modules 37, and application data 38 are loaded for execution by processors 20. Volatile memory 30b is generally faster than non-volatile memory 30a due to its electrical characteristics and is directly accessible to processors 20 for processing of instructions and data storage and retrieval. Volatile memory 30b may comprise one or more smaller cache memories which operate at a higher clock speed and are typically placed on the same IC as the processors to improve performance.

Interfaces 40 may include, but are not limited to, storage media interfaces 41, network interfaces 42, display interfaces 43, and input/output interfaces 44. Storage media interface 41 provides the necessary hardware interface for loading data from non-volatile data storage devices 50 into system memory 30 and storage data from system memory 30 to non-volatile data storage device 50. Network interface 42 provides the necessary hardware interface for computing device 10 to communicate with remote computing devices 80 and cloud-based services 90 via one or more external communication devices 70. Display interface 43 allows for connection of displays 61, monitors, touchscreens, and other visual input/output devices. Display interface 43 may include a graphics card for processing graphics-intensive calculations and for handling demanding display requirements. Typically, a graphics card includes a graphics processing unit (GPU) and video RAM (VRAM) to accelerate display of graphics. One or more input/output (I/O) interfaces 44 provide the necessary support for communications between computing device 10 and any external peripherals and accessories 60. For wireless communications, the necessary radio-frequency hardware and firmware may be connected to I/O interface 44 or may be integrated into I/O interface 44.

Non-volatile data storage devices 50 are typically used for long-term storage of data. Data on non-volatile data storage devices 50 is not erased when power to the non-volatile data storage devices 50 is removed. Non-volatile data storage devices 50 may be implemented using any technology for non-volatile storage of content including, but not limited to, CD-ROM drives, digital versatile discs (DVD), or other optical disc storage; magnetic cassettes, magnetic tape, magnetic disc storage, or other magnetic storage devices; solid state memory technologies such as EEPROM or flash memory; or other memory technology or any other medium which can be used to store data without requiring power to retain the data after it is written. Non-volatile data storage devices 50 may be non-removable from computing device 10 as in the case of internal hard drives, removable from computing device 10 as in the case of external USB hard drives, or a combination thereof, but computing device will typically comprise one or more internal, non-removable hard drives using either magnetic disc or solid state memory technology. Non-volatile data storage devices 50 may store any type of data including, but not limited to, an operating system 51 for providing low-level and mid-level functionality of computing device 10, applications 52 for providing high-level functionality of computing device 10, program modules 53 such as containerized programs or applications, or other modular content or modular programming, application data 54, and databases 55 such as relational databases, non-relational databases, and graph databases.

Applications (also known as computer software or software applications) are sets of programming instructions designed to perform specific tasks or provide specific functionality on a computer or other computing devices. Applications are typically written in high-level programming languages such as C++, Java, and Python, which are then either interpreted at runtime or compiled into low-level, binary, processor-executable instructions operable on processors 20. Applications may be containerized so that they can be run on any computer hardware running any known operating system. Containerization of computer software is a method of packaging and deploying applications along with their operating system dependencies into self-contained, isolated units known as containers. Containers provide a lightweight and consistent runtime environment that allows applications to run reliably across different computing environments, such as development, testing, and production systems.

The memories and non-volatile data storage devices described herein do not include communication media. Communication media are means of transmission of information such as modulated electromagnetic waves or modulated data signals configured to transmit, not store, information. By way of example, and not limitation, communication media includes wired communications such as sound signals transmitted to a speaker via a speaker wire, and wireless communications such as acoustic waves, radio frequency (RF) transmissions, infrared emissions, and other wireless media.

External communication devices 70 are devices that facilitate communications between computing device and either remote computing devices 80, or cloud-based services 90, or both. External communication devices 70 include, but are not limited to, data modems 71 which facilitate data transmission between computing device and the Internet 75 via a common carrier such as a telephone company or internet service provider (ISP), routers 72 which facilitate data transmission between computing device and other devices, and switches 73 which provide direct data communications between devices on a network. Here, modem 71 is shown connecting computing device 10 to both remote computing devices 80 and cloud-based services 90 via the Internet 75. While modem 71, router 72, and switch 73 are shown here as being connected to network interface 42, many different network configurations using external communication devices 70 are possible. Using external communication devices 70, networks may be configured as local area networks (LANs) for a single location, building, or campus, wide area networks (WANs) comprising data networks that extend over a larger geographical area, and virtual private networks (VPNs) which can be of any size but connect computers via encrypted communications over public networks such as the Internet 75. As just one exemplary network configuration, network interface 42 may be connected to switch 73 which is connected to router 72 which is connected to modem 71 which provides access for computing device 10 to the Internet 75. Further, any combination of wired 77 or wireless 76 communications between and among computing device 10, external communication devices 70, remote computing devices 80, and cloud-based services 90 may be used. Remote computing devices 80, for example, may communicate with computing device through a variety of communication channels 74 such as through switch 73 via a wired 77 connection, through router 72 via a wireless connection 76, or through modem 71 via the Internet 75. Furthermore, while not shown here, other hardware that is specifically designed for servers may be employed. For example, secure socket layer (SSL) acceleration cards can be used to offload SSL encryption computations, and transmission control protocol/internet protocol (TCP/IP) offload hardware and/or packet classifiers on network interfaces 42 may be installed and used at server devices.

In a networked environment, certain components of computing device 10 may be fully or partially implemented on remote computing devices 80 or cloud-based services 90. Data stored in non-volatile data storage device 50 may be received from, shared with, duplicated on, or offloaded to a non-volatile data storage device on one or more remote computing devices 80 or in a cloud computing service 92. Processing by processors 20 may be received from, shared with, duplicated on, or offloaded to processors of one or more remote computing devices 80 or in a distributed computing service 93. By way of example, data may reside on a cloud computing service 92, but may be usable or otherwise accessible for use by computing device 10. Also, certain processing subtasks may be sent to a microservice 91 for processing with the result being transmitted to computing device 10 for incorporation into a larger processing task. Also, while components and processes of the exemplary computing environment are illustrated herein as discrete units (e.g., OS 51 being stored on non-volatile data storage device 51 and loaded into system memory 35 for use) such processes and components may reside or be processed at various times in different components of computing device 10, remote computing devices 80, and/or cloud-based services 90.

Remote computing devices 80 are any computing devices not part of computing device 10. Remote computing devices 80 include, but are not limited to, personal computers, server computers, thin clients, thick clients, personal digital assistants (PDAs), mobile telephones, watches, tablet computers, laptop computers, multiprocessor systems, microprocessor based systems, set-top boxes, programmable consumer electronics, video game machines, game consoles, portable or handheld gaming units, network terminals, desktop personal computers (PCs), minicomputers, main frame computers, network nodes, and distributed or multi-processing computing environments. While remote computing devices 80 are shown for clarity as being separate from cloud-based services 90, cloud-based services 90 are implemented on collections of networked remote computing devices 80.

Cloud-based services 90 are Internet-accessible services implemented on collections of networked remote computing devices 80. Cloud-based services are typically accessed via application programming interfaces (APIs) which are software interfaces which provide access to computing services within the cloud-based service via API calls, which are pre-defined protocols for requesting a computing service and receiving the results of that computing service. While cloud-based services may comprise any type of computer processing or storage, three common categories of cloud-based services 90 are microservices 91, cloud computing services 92, and distributed computing services 93.

Microservices 91 are collections of small, loosely coupled, and independently deployable computing services. Each microservice represents a specific computing functionality and runs as a separate process or container. Microservices promote the decomposition of complex applications into smaller, manageable services that can be developed, deployed, and scaled independently. These services communicate with each other through well-defined application programming interfaces (APIs), typically using lightweight protocols like HTTP or message queues. Microservices 91 can be combined to perform more complex processing tasks.

Cloud computing services 92 are delivery of computing resources and services over the Internet 75 from a remote location. Cloud computing services 92 provide additional computer hardware and storage on as-needed or subscription basis. Cloud computing services 92 can provide large amounts of scalable data storage, access to sophisticated software and powerful server-based processing, or entire computing infrastructures and platforms. For example, cloud computing services can provide virtualized computing resources such as virtual machines, storage, and networks, platforms for developing, running, and managing applications without the complexity of infrastructure management, and complete software applications over the Internet on a subscription basis.

Distributed computing services 93 provide large-scale processing using multiple interconnected computers or nodes to solve computational problems or perform tasks collectively. In distributed computing, the processing and storage capabilities of multiple machines are leveraged to work together as a unified system. Distributed computing services are designed to address problems that cannot be efficiently solved by a single computer or that require large-scale computational power. These services enable parallel processing, fault tolerance, and scalability by distributing tasks across multiple nodes.

Although described above as a physical device, computing device 10 can be a virtual computing device, in which case the functionality of the physical components herein described, such as processors 20, system memory 30, network interfaces 40, and other like components can be provided by computer-executable instructions. Such computer-executable instructions can execute on a single physical computing device, or can be distributed across multiple physical computing devices, including being distributed across multiple physical computing devices in a dynamic manner such that the specific, physical computing devices hosting such computer-executable instructions can dynamically change over time depending upon need and availability.

In the situation where computing device 10 is a virtualized device, the underlying physical computing devices hosting such a virtualized computing device can, themselves, comprise physical components analogous to those described above, and operating in a like manner. Furthermore, virtual computing devices can be utilized in multiple layers with one virtual computing device executing within the construct of another virtual computing device. Thus, computing device 10 may be either a physical computing device or a virtualized computing device within which computer-executable instructions can be executed in a manner consistent with their execution by a physical computing device. Similarly, terms referring to physical components of the computing device, as utilized herein, mean either those physical components or virtualizations thereof performing the same or equivalent functions.

The skilled person will be aware of a range of possible modifications of the various aspects described above. Accordingly, the present invention is defined by the claims and their equivalents.

What is claimed is:

1. A system for upsampling of decompressed biological data after lossy compression using a neural network, comprising:

a computing system comprising at least a memory and a processor;

two or more datasets that are substantially correlated and which have been compressed with lossy compression, the two or more datasets comprising biological data;

a deep learning neural network configured to recover lost information associated with a compressed bit stream; and a decoder comprising a first plurality of programming instructions that, when operating on the processor, cause the computing system to:

receive a compressed bit stream, the compressed bit stream comprising cross-correlated biological data;

decompress each of the compressed bit stream; and use the decompressed bit stream as an input into the deep learning neural network to recover lost information associated with the biological data.

2. The system of claim 1, wherein the biological data comprises parallel biological datasets.

3. The system of claim 1, wherein the two or more datasets comprise genomic data from a subset of the human genome.

4. The system of claim 1, wherein the deep learning neural network is a neural network that can recover signals from a compressed bitstream.

5. The system of claim 1, wherein the compressed bit stream comprises a plurality of channels, wherein each of the plurality of channels is associated with a genomic dataset.

6. A method for upsampling of decompressed biological data after lossy compression using a neural network, comprising the steps of:

training a deep learning neural network to recover lost information associated with a compressed bit stream;

receiving the compressed bit stream, the compressed bit stream comprising cross-correlated biological data;

decompressing the compressed bit stream; and using the decompressed bit stream as an input into the deep learning neural network to recover information lost during lossy compression of the biological data.

7. The method of claim 6, wherein the biological data comprises parallel biological datasets.

8. The method of claim 6, wherein the two or more datasets comprise genomic data from a subset of the human genome.

9. The method of claim 6, wherein the deep learning neural network is a neural network that can recover signals from a compressed bitstream.

10. The method of claim 6, wherein the compressed bit stream comprises a plurality of channels, wherein each of the plurality of channels is associated with a genomic dataset.

11. One or more non-transitory computer-storage media having computer-executable instructions embodied thereon that, when executed by one or more processors of a computing system employing a neural upsampler configured for biological data, cause the computing system to perform the method of claim 6.

* * * * *